(12) United States Patent (10) Patent No.: US 9,060,113 B2
Rhoads et al. (45) Date of Patent: Jun. 16, 2015

(54) SENSOR-SYNCHRONIZED SPECTRALLY-STRUCTURED-LIGHT IMAGING

(71) Applicant: Digimarc Corporation, Beaverton, OR (US)

(72) Inventors: Geoffrey B. Rhoads, West Linn, OR (US); Tony F. Rodriguez, Portland, OR (US)

(73) Assignee: Digimarc Corporation, Beaverton, OR (US)

( * ) Notice: Subject to any disclaimer, the term of this patent is extended or adjusted under 35 U.S.C. 154(b) by 0 days.

(21) Appl. No.: 13/840,451

(22) Filed: Mar. 15, 2013

(65) Prior Publication Data

US 2013/0308045 A1 Nov. 21, 2013

Related U.S. Application Data

(60) Provisional application No. 61/688,722, filed on May 21, 2012, provisional application No. 61/706,982, filed on Sep. 28, 2012.

(51) Int. Cl.
| | |
|---|---|
| *H04N 5/222* | (2006.01) |
| *H04N 5/225* | (2006.01) |
| *G01J 3/51* | (2006.01) |
| *A61B 5/00* | (2006.01) |
| *G01J 3/28* | (2006.01) |
| *G01J 3/36* | (2006.01) |
| *H04N 5/235* | (2006.01) |

(52) U.S. Cl.
CPC .............. *H04N 5/2256* (2013.01); *G01J 3/513* (2013.01); *A61B 5/6898* (2013.01); *A61B 5/0075* (2013.01); *G01J 3/2823* (2013.01); *G01J 3/36* (2013.01); *G01J 3/51* (2013.01); *H04N 5/2354* (2013.01)

(58) Field of Classification Search
None
See application file for complete search history.

(56) References Cited

U.S. PATENT DOCUMENTS

| | | | |
|---|---|---|---|
| 6,069,696 | A | 5/2000 | McQueen et al. |
| 6,363,366 | B1 | 3/2002 | Henty |
| 6,466,961 | B1 | 10/2002 | Miller |

(Continued)

FOREIGN PATENT DOCUMENTS

| | | |
|---|---|---|
| FR | 2905185 | 2/2008 |
| WO | WO2008152922 | 12/2008 |

(Continued)

OTHER PUBLICATIONS

Gat, Imaging spectroscopy using tunable filters—a review, *AeroSense 2000*, International Society for Optics and Photonics, Proc. SPIE vol. 4056, p. 50-64.

(Continued)

*Primary Examiner* — Sinh Tran
*Assistant Examiner* — Shahbaz Nazrul
(74) *Attorney, Agent, or Firm* — Digimarc Corporation

(57) ABSTRACT

A smartphone is adapted for use as an imaging spectrometer, by synchronized pulsing of different LED light sources as different image frames are captured by the phone's CMOS image sensor. A particular implementation employs the CIE color matching functions, and/or their orthogonally transformed functions, to enable direct chromaticity capture. A great variety of other features and arrangements are also detailed.

12 Claims, 38 Drawing Sheets
(35 of 38 Drawing Sheet(s) Filed in Color)

(56) References Cited

U.S. PATENT DOCUMENTS

| | | |
|---|---|---|
| 7,319,990 B1 | 1/2008 | Henty |
| 7,393,119 B2 | 7/2008 | Lebens et al. |
| 7,420,663 B2 | 9/2008 | Wang et al. |
| 7,667,766 B2 | 2/2010 | Lee et al. |
| 7,995,911 B2 | 8/2011 | Butterworth |
| 8,284,279 B2 | 10/2012 | Park et al. |
| 8,358,089 B2 | 1/2013 | Hsia et al. |
| 8,364,031 B2 | 1/2013 | Geffert et al. |
| 8,385,971 B2 | 2/2013 | Rhoads et al. |
| 2002/0001080 A1 | 1/2002 | Miller et al. |
| 2005/0030416 A1 | 2/2005 | Kametani et al. |
| 2005/0030533 A1 | 2/2005 | Treado |
| 2006/0133061 A1 | 6/2006 | Maeda |
| 2006/0161788 A1 | 7/2006 | Turpin et al. |
| 2006/0202028 A1 | 9/2006 | Rowe et al. |
| 2008/0133389 A1 | 6/2008 | Schowengerdt et al. |
| 2008/0177185 A1 | 7/2008 | Nakao et al. |
| 2008/0297644 A1* | 12/2008 | Farchtchian et al. ......... 348/340 |
| 2009/0067695 A1* | 3/2009 | Komiya et al. ............ 382/128 |
| 2009/0112101 A1 | 4/2009 | Furness, III et al. |
| 2010/0042004 A1 | 2/2010 | Dhawan |
| 2010/0048242 A1 | 2/2010 | Rhoads et al. |
| 2010/0073504 A1 | 3/2010 | Park et al. |
| 2010/0208240 A1 | 8/2010 | Schowengerdt et al. |
| 2011/0069443 A1* | 3/2011 | Williams ................ 361/679.33 |
| 2011/0090485 A1 | 4/2011 | Cronin et al. |
| 2011/0123185 A1* | 5/2011 | Clark ............................ 396/198 |
| 2011/0176029 A1 | 7/2011 | Boydston et al. |
| 2011/0249911 A1 | 10/2011 | Determan et al. |
| 2011/0293184 A1 | 12/2011 | Silverbrook et al. |
| 2011/0304705 A1 | 12/2011 | Kantor et al. |
| 2012/0224042 A1 | 9/2012 | Saijo |
| 2012/0307081 A1 | 12/2012 | Dewald et al. |
| 2012/0307137 A1* | 12/2012 | Chuang et al. ................ 348/371 |
| 2012/0321759 A1 | 12/2012 | Marinkovich et al. |
| 2013/0195273 A1 | 8/2013 | Lord |
| 2013/0215168 A1 | 8/2013 | Furness, III et al. |
| 2013/0215596 A1 | 8/2013 | Holman et al. |
| 2013/0259320 A1 | 10/2013 | Gotanda |
| 2013/0332367 A1 | 12/2013 | Quigley et al. |
| 2014/0063239 A1 | 3/2014 | Furness, III et al. |
| 2014/0085534 A1* | 3/2014 | Bergquist ..................... 348/371 |
| 2014/0233015 A1 | 8/2014 | Mander et al. |

FOREIGN PATENT DOCUMENTS

| | | |
|---|---|---|
| WO | WO2011017550 | 2/2011 |
| WO | WO2012002787 | 1/2012 |
| WO | WO2012020381 | 2/2012 |
| WO | WO2013098708 | 7/2013 |

OTHER PUBLICATIONS

Hayes, Next-generation cell phone cameras, *Optics and Photonics News* 23.2 (2012), pp. 16-21.

Karlen, et al, Design challenges for camera oximetry on a mobile phone, 2012 Annual Int'l Conference of IEEE Engineering in Medicine and Biology Society.

Park, et al, Multispectral imaging using multiplexed illumination, 11th IEEE Int'l Conf on Computer Vision, 2007.

Tominaga, et al, Spectral imaging by synchronizing capture and illumination, JOSA A 29.9 (2012), pp. 1764-1775.

Bolle, et al, VeggieVision: A Produce Recognition System, 1996.

Chi, et al, Multi-spectral imaging by optimized wide band illumination, International Journal of Computer Vision 86.2-3 (2010), pp. 140-151.

Everdell, et al, Multispectral imaging of the ocular fundus using LED illumination, European Conference on Biomedical Optics, Optical Society of America, 2009.

Han, et al Fast Spectral Reflectance Recovery Using DLP Projector, Computer Vision—ACCV, pp. 323-335, 2010.

Kawakami, et al, High-Resolution Hyperspectral Imaging via Matrix Factorization, IEEE Conf. on Computer Vision and Pattern Recognition (CVPR) 2011.

Lee et al, Fast Model-Based Multi-Spectral Imaging Using Nonnegative Principal Component Analysis, Optics Letters, vol. 37, No. 11, Jun. 1, 2012, pp. 1937-1939.

Nieves, et al., Multispectral synthesis of daylight using a commercial digital CCD camera, Applied Optics 44.27 (2005): 5696-5703.

Park, et al., Multispectral imaging using multiplexed illumination, IEEE Int'l Conf on Computer Vision, 2007.

PCT International Search Report and Written Opinion of the International Searching Authority, PCT/US2013/040392 (published as WO2013176900), Nov. 28, 2013.

Richards, et al, Low-cost laser speckle contrast imaging of blood flow using a webcam, Biomedical Optics Express 4.10 (2013), pp. 2269-2283.

Schockling, et al, Visualization of hyperspectral images, SPIE Defense, Security, and Sensing, 2009.

Shrestha, et al, LED Based Multispectral Film Scanner for Accurate Color Imaging, IEEE Eighth International Conference on Signal Image Technology and Internet Based Systems, 2012.

Solovchenko, et al, Non-destructive estimation pigment content ripening quality and damage in apple fruit with spectral reflectance in the visible range, Global Science Books, 2010.

Nature's Color Identifier, The ChromaID Story, Visualant, Jan. 24, 2013.

* cited by examiner

Flexibility on the Sensor-side

460: sample digital camera pixel-response spectral profiles

Even more flexibility on the
LED spectral-shape side   (cont.)

Examples of the ability to design spectral shapes aimed at certain applications, this one for Flourescence Microscopy More Analytic Dental Imaging Example Medical Applications Endoscopy Diagnostic Improvement $$\Delta d_{red} = \sum_i Red_i(A_i + L1_i)R_i - \sum_i Red_i A_i R_i = \sum_i Red_i L1_i R_i$$

$$\Delta d_{green} = \sum_i Green_i(A_i + L1_i)R_i - \sum_i Green_i A_i R_i = \sum_i Green_i L1_i R_i$$

$$\Delta d_{blue} = \sum_i Blue_i(A_i + L1_i)R_i - \sum_i Blue_i A_i R_i = \sum_i Blue_i L1_i R_i$$

FIGURE 37

SENSOR-SYNCHRONIZED SPECTRALLY-STRUCTURED-LIGHT IMAGING

RELATED APPLICATION DATA

This application is a non-provisional of copending provisional applications 61/688,722, filed May 21, 2012, and 61/706,982, filed Sep. 28, 2012.

TECHNICAL FIELD

The present technology concerns, e.g., imaging spectrometry.

BACKGROUND AND INTRODUCTION OF THE TECHNOLOGY

Both natural light ('ambient') photography and flash-assisted (read broadly: 'human assisted light supplementation') photography have been around since the Daguerreotype. The present technology concerns how primarily the latter form of lighting, call it 'flash' for conciseness, can be so designed and implemented as to effectively qualify it within the general art of 'imaging spectrometry' or 'hyper-spectral imaging.'

In a nutshell, by illuminating a scene with several different brief (frame-synchronized) 'spectrally structured' light sources, even a common Bayer pattern CMOS camera can effectively become an imaging spectrometer with 'N bands,' N in very early days being practically on the order of 5 to 10 bands, but with fine prospects of going higher, especially as design principles behind Bayer patterns (and RGBW, e.g., from Sony) are reconsidered in light of this technology.

An introduction of the technology must make note of multi-chip LEDs (see e.g. Edison's 2012-era Federal FM series, depicted in FIG. 7) as being at least a seed for just what the doctor ordered regarding 'spectrally structured light.' A core idea—and current preferred embodiment—is to synchronize pulsing of different LED light sources with individual frames of a CMOS sensor, thereby creating the informational basis for N-band imaging. Light sources other than LEDs can certainly be considered but by 2012 standards, multi-chip and/or 'dual' LEDs are leading candidates to realize this technology.

A particularly intriguing choice of 'bands' is the 3 very well-known 1931 CIE color matching functions and/or their orthogonally transformed functions. With such choices, the stage is set for taking the beyond-religiously-fervent universe of color photography to its multiverse destiny: blandly referred to as 'direct chromaticity capture' in this disclosure.

The bulk of this disclosure zooms in on the design principles and physical realizations of turning virtually any electronic imaging sensor into an imaging spectrometer via specific coordination with some supplemental light source. With the core 'how' then elucidated, four essentially discrete applications will be presented and described, including A) the niche application of hyper-spectral imaging, B) the medical imaging potential of this technology, C) the previously alluded-to culturally-volatile topic of radically improved color photography for both 'digital cameras' and smart phones (as 2012 still draws pretty sharp lines between the two), and D) uses of N-band imaging within the mature technology of digital watermarking and 'image fingerprinting.'

The foregoing and other features and advantages of the present technology will be more readily apparent from the following Detailed Description, which proceeds with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 37 details how unknown ambient lighting spectral coefficients can be removed from aggregate mathematical equations.

Figure 1:
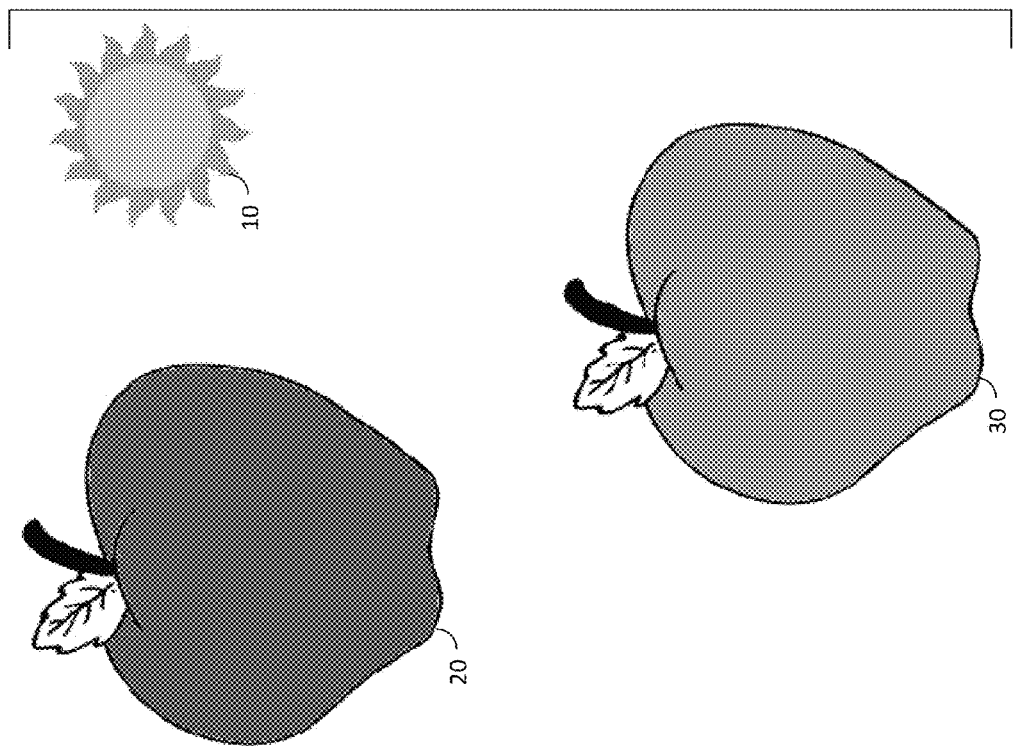
FIG. 1 illustrates how most modern cameras distinguish red apples from green apples.
Figure 1:
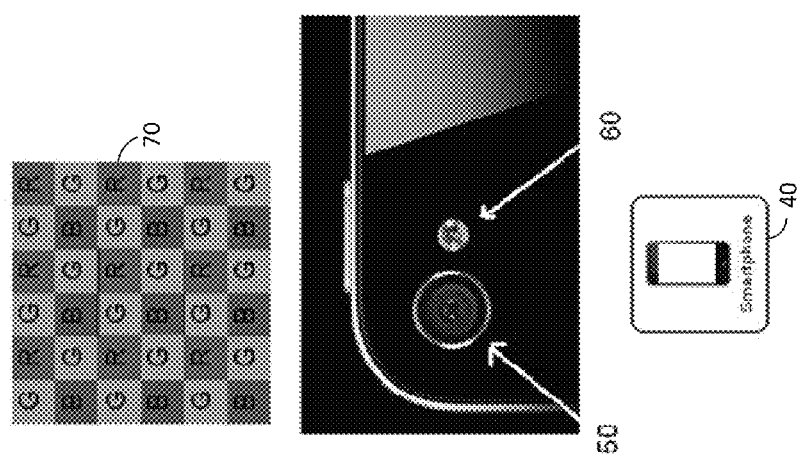

In compliance with Patent Office requirements, certain excessive text was moved from certain of the figures into the specification. That text is presented below:

FIG. 1 shows, at 70, a classic "Bayer Pattern," typifying the color filter arrangements of the individual pixels of a modern CMOS camera. Below is shown part of a 2012-era smartphone 40, with a CMOS camera aperture 50, and an LED flash aperture 60. Also shown are two apples, a red apple 20 and a green apple 30, respectively reflecting red and green light from the sun 10 (which produces "white light" ambient illumination).

Figure 3:
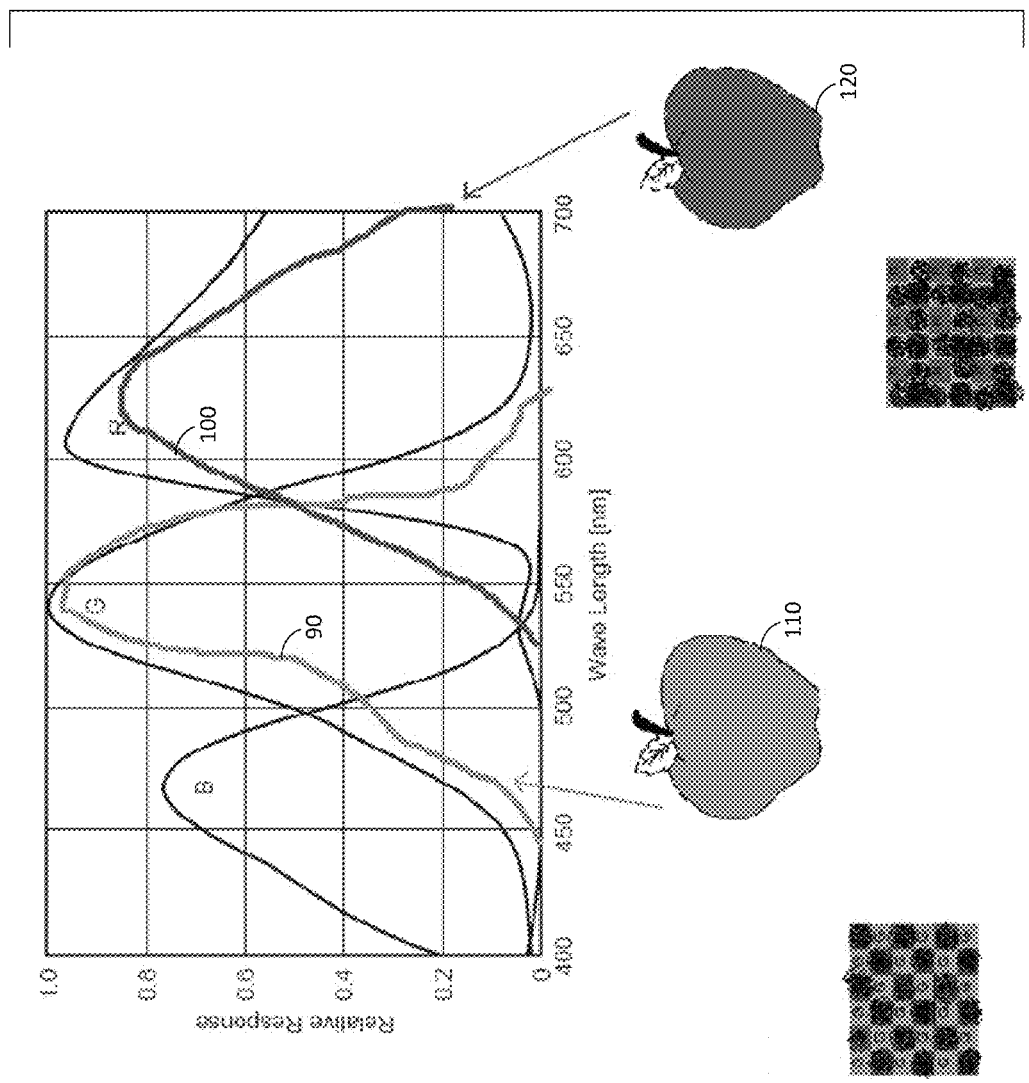
FIG. 3 is similar to FIG. 1, but includes information about an idealized spectral reflectance profile of a green apple, and of a red apple.

FIG. 3 shows how the spectral reflectance profile, 90, of the green apple might nicely mimic the Bayer-pixel spectral profile of the "G" channel. In the lower left, the "G" channel pixels "light up" whilst imaging the green apple 110. Likewise, the spectral reflectance profile 100 of the red apple might nicely mimic the Bayer-pixel spectral profile of the "R" channel. In the lower right, the "R" channel pixels "light up" when imaging the red apple 120.

Figure 4:
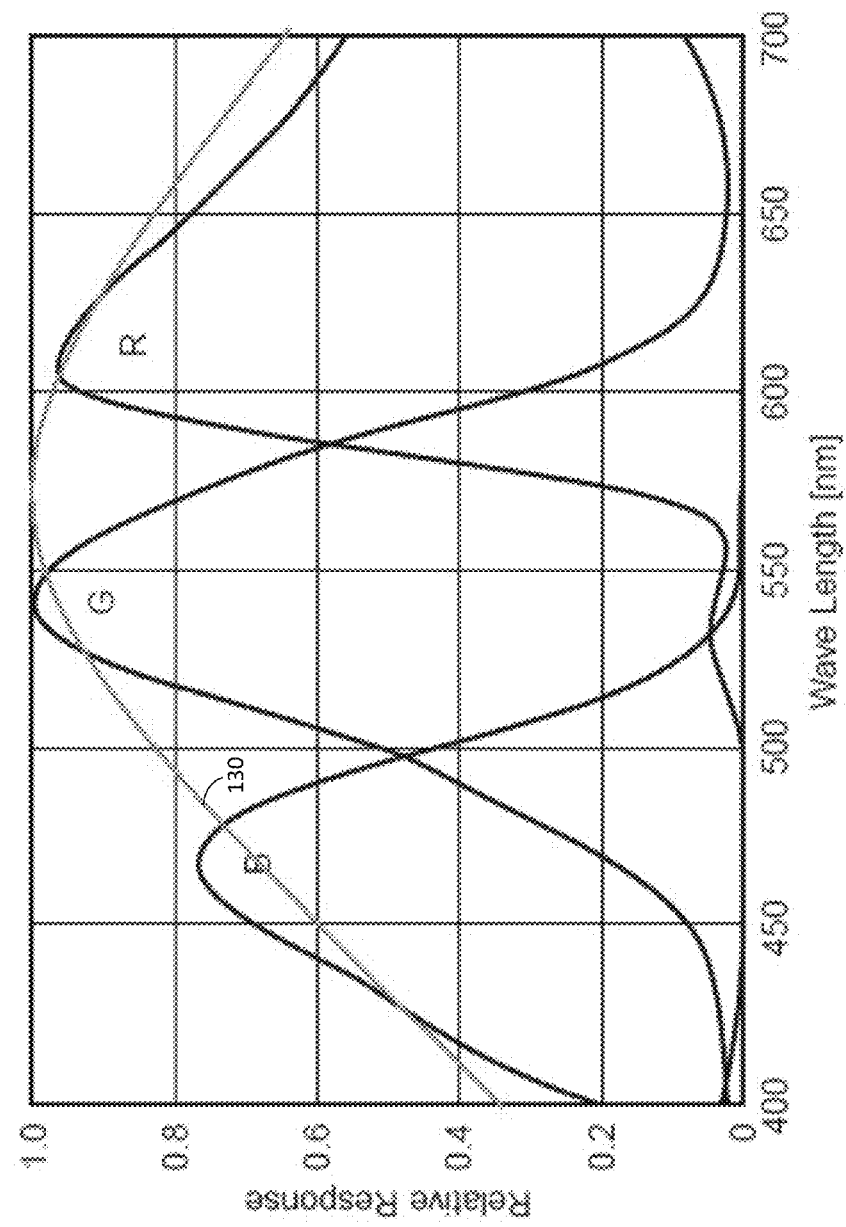
FIG. 4 introduces an idealized ambient lighting source spectral curve.

FIG. 4 concerns the fact that a scene is effectively never illuminated with strictly "white light." There is always a "structure" to the light spectral curve—illustrated in very simple fashion in this figure. In particular, curve 130 shows the "actual" but largely "unknown" ambient lighting spectral profile of a scene (the apples).

Figure 5:
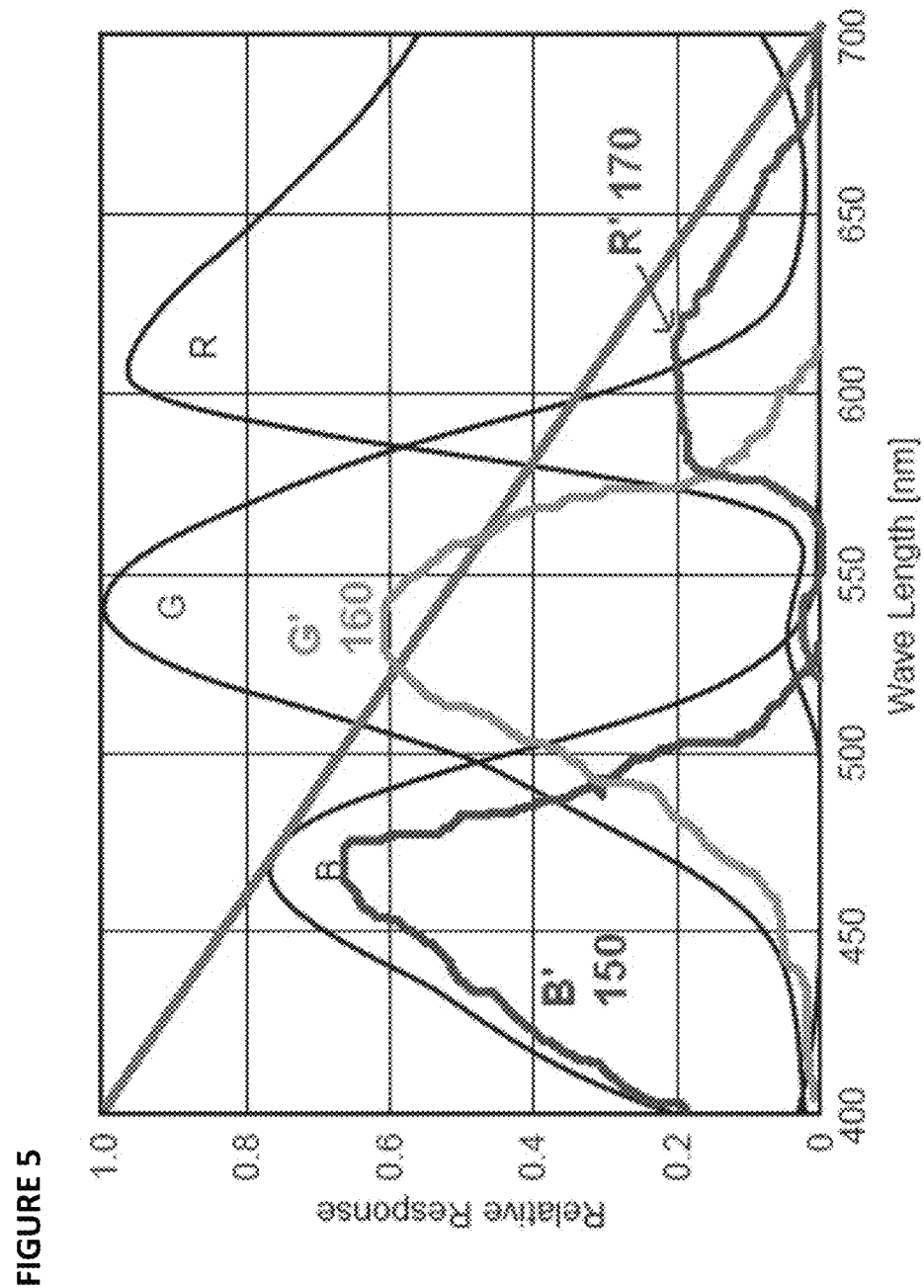
FIG. 5 presents a case involving slight green-ish, mainly blue-ish illumination.

FIG. 5 illustrates a hypothetical "slight green-ish, mainly blue-ish" light source, 140, giving rise to "lighting modified" effective spectral response curves B', 140, G', 160 and R' 170.

Figure 6:
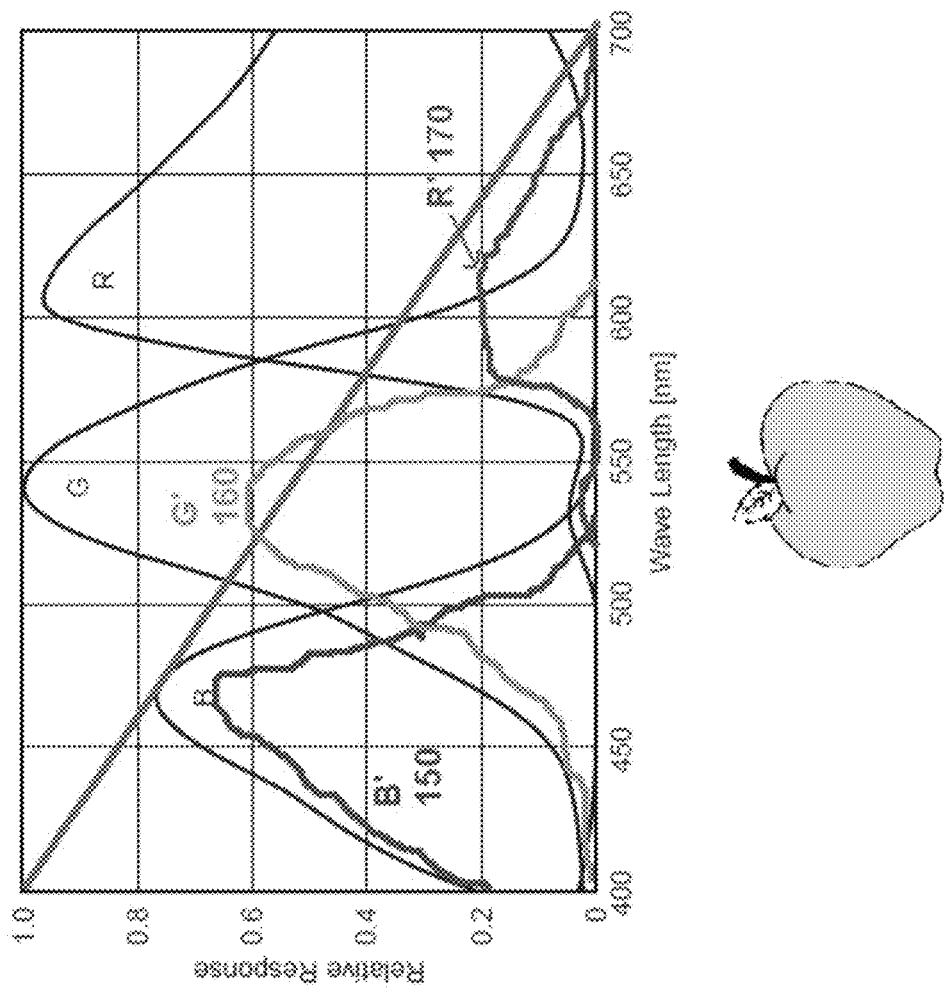
FIG. 6 shows how an apple may be mis-colored when rendered on a screen, due to illumination.

FIG. 6 shows how the red apple will "look" yellowish, 180—a pretty even combination of green and red—under the lighting conditions of the previous figure, all because of the different lighting and nothing to do with the sensors. The "effective" profiles B', G' and R' all get shaped by the knowable characteristics of the lighting.

Figure 7:
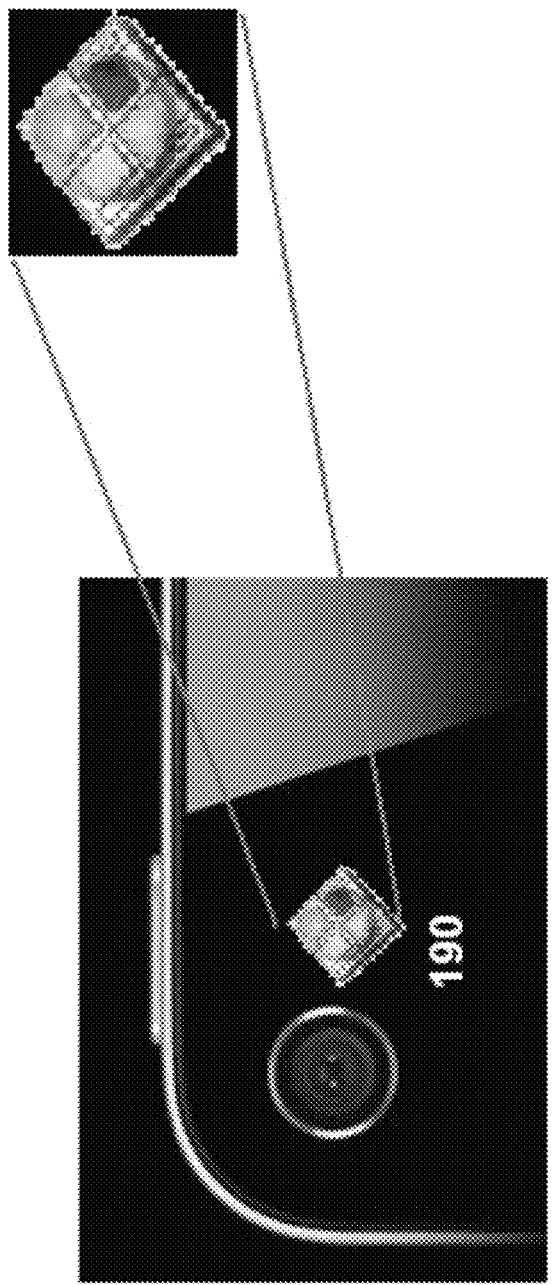
FIGS. 7 and 8 introduce the notion of multi-colored flash.

FIG. 7 shows that the "standard white" LEDs found in existing camera phone flashes can be replaced with so-called "Multichip LEDs," with the Edison Corporation Federal FM series model here depicted (190).

Figure 8:
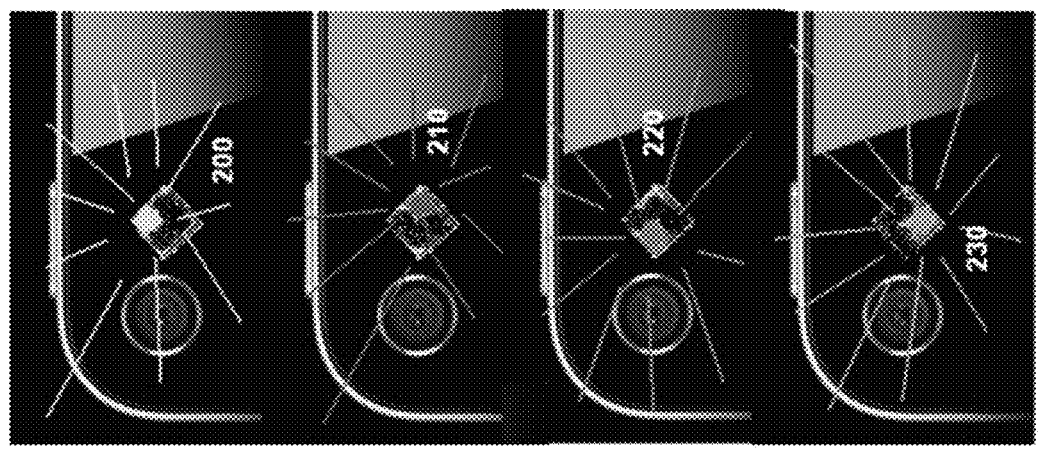

FIG. 8 shows how all of this, to the human eye, looks like a pretty funky pseudo-strobe kind of white light illumination since it is cycling so quickly. In particular, starting with the top, coordinated with frame 4*n (n continuously increasing), one of the LED flashes for typically ⅓₀th of a second, 200, for example with a yellow-ish light, yet well known spectrally. Below, sensor frame 4*n+1 then coordinates with another LED flashing for ⅓₀th of a second, 210, this time with a redish looking light, again with well known spectral characteristics. Then below, frame 4*n+2 witnesses a purplish LEF flash, 220, tending more toward the bluish and green side of the spectrum. Finally, at the bottom, frame 4*n+3 has a mauvish LED flash with its exposure time of ⅓₀th of a second, completing the flash cycle and then incrementing "n" to go back to the top for movies, or stop for a single "image" capture (i.e., n=1 and only 1 for a single image).

Figure 11:
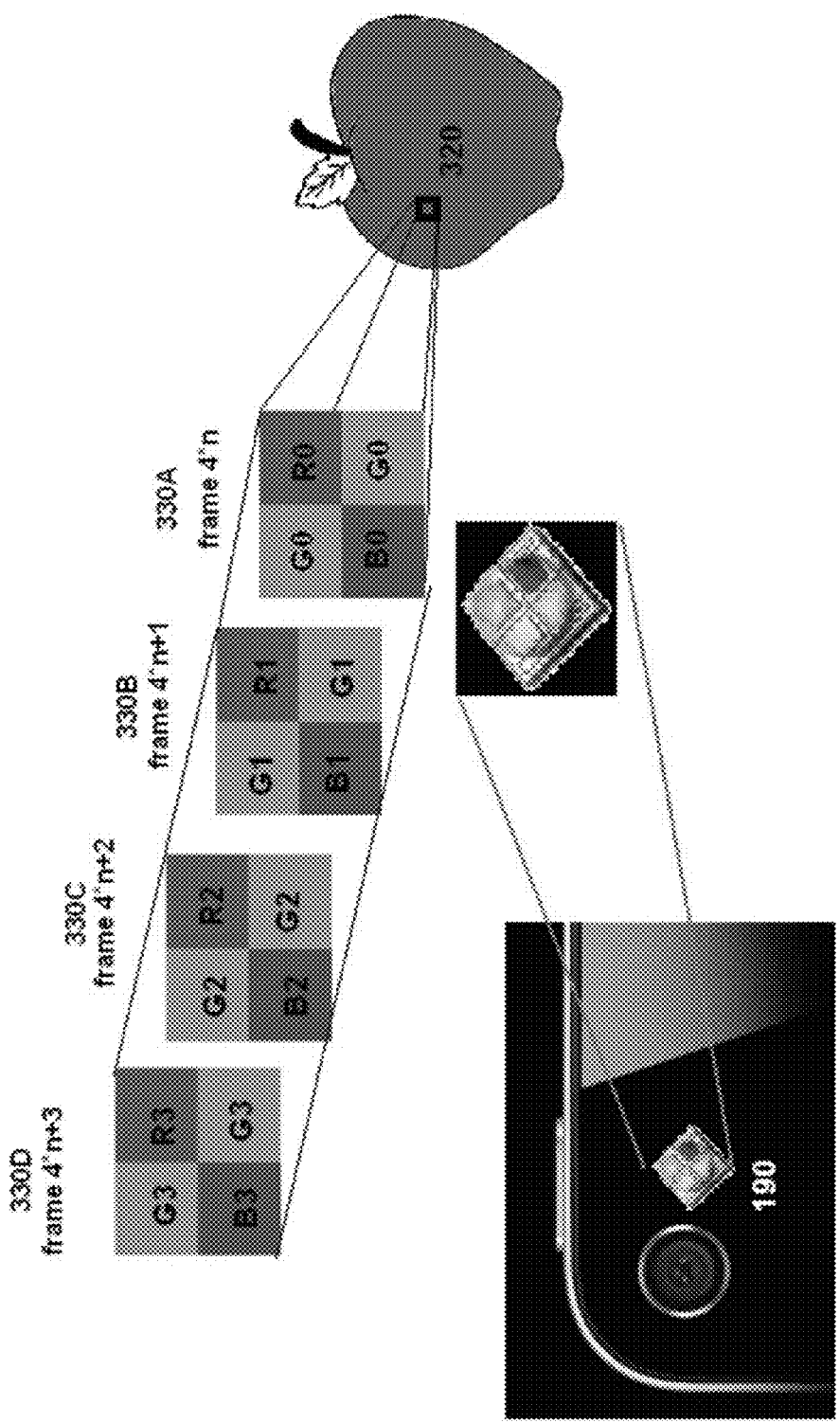
FIG. 11 illustrates different spectral samplings of an apple.

FIG. 11 illustrates how some small patch on the red apple, 320, corresponding to a Bayer cell, 330A-D, thus has effectively 12 different "spectral samplings" measured over four frames of image data, corresponding to B0, B1, B2, B3, G0, G1, G2, G3, R0, R1, R2 and R3. The Bayer cell is the same physical cell for all four frames, but with different lighting they have different effective spectral sampling profiles.

Figure 12:
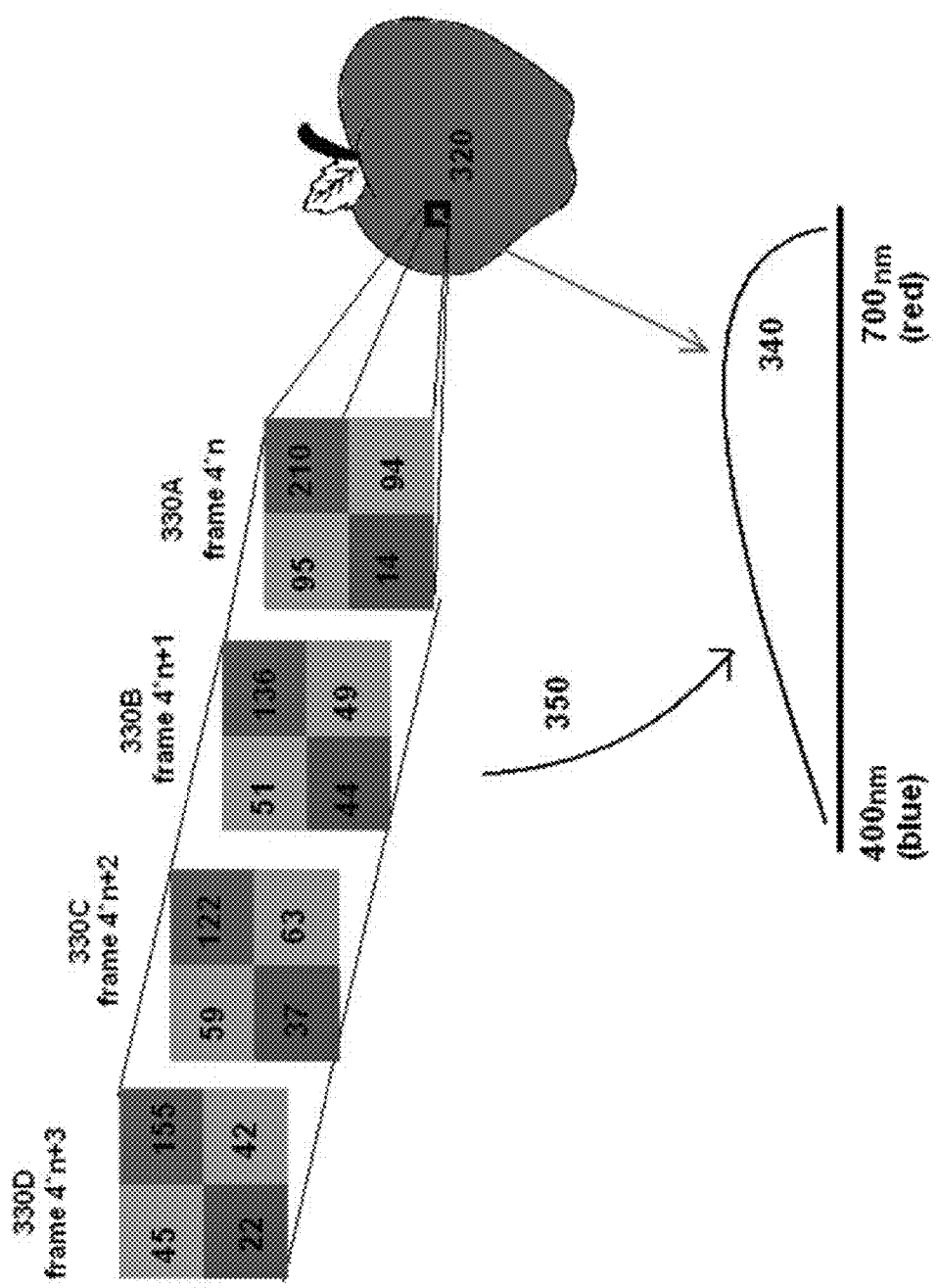
FIG. 12 illustrates how data gathered in FIG. 11 can be used to produce spectral information for the apple.

FIG. 12 examines how this sequence of digitized pixel values lets us try to measure the "unknown" spectral reflection function of the patch of apple being imaged, including a hypothetical "actual" spectral reflectance function 340 of the patch of apple 320.

Figure 13:
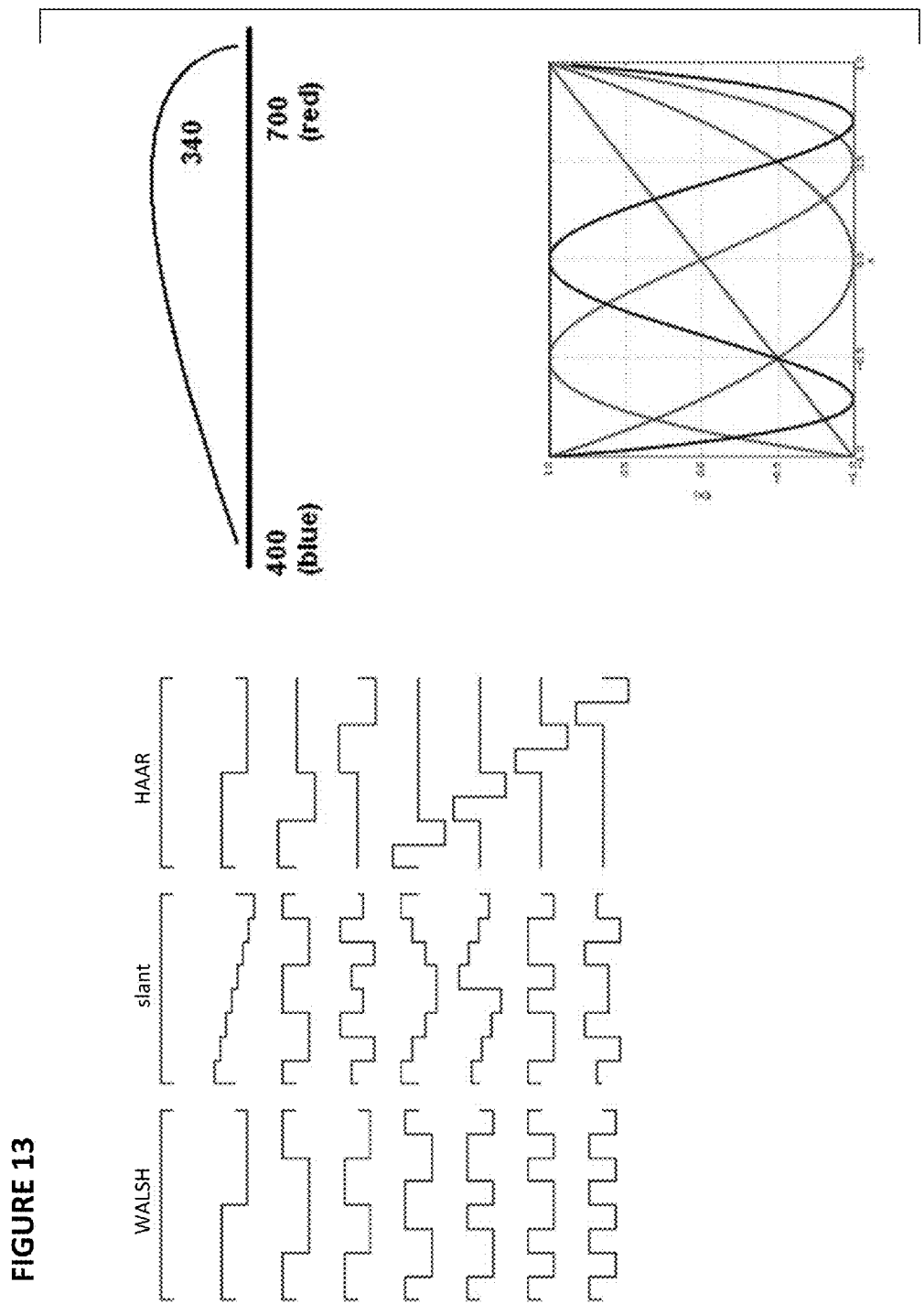
FIG. 13 shows a linear function estimation arrangement that can be used with the spectral information of FIG. 12.

FIG. 13 concerns generic linear functional estimation. The left side shows typical examples of orthogonal discrete functions often used to parameterize (fit) unknown distributions (the apple's true reflectance spectrum 340 in our example).

The lower right shows that "smooth" functions can similarly be used, a la Chebyschev Polynomials.

Figure 14:
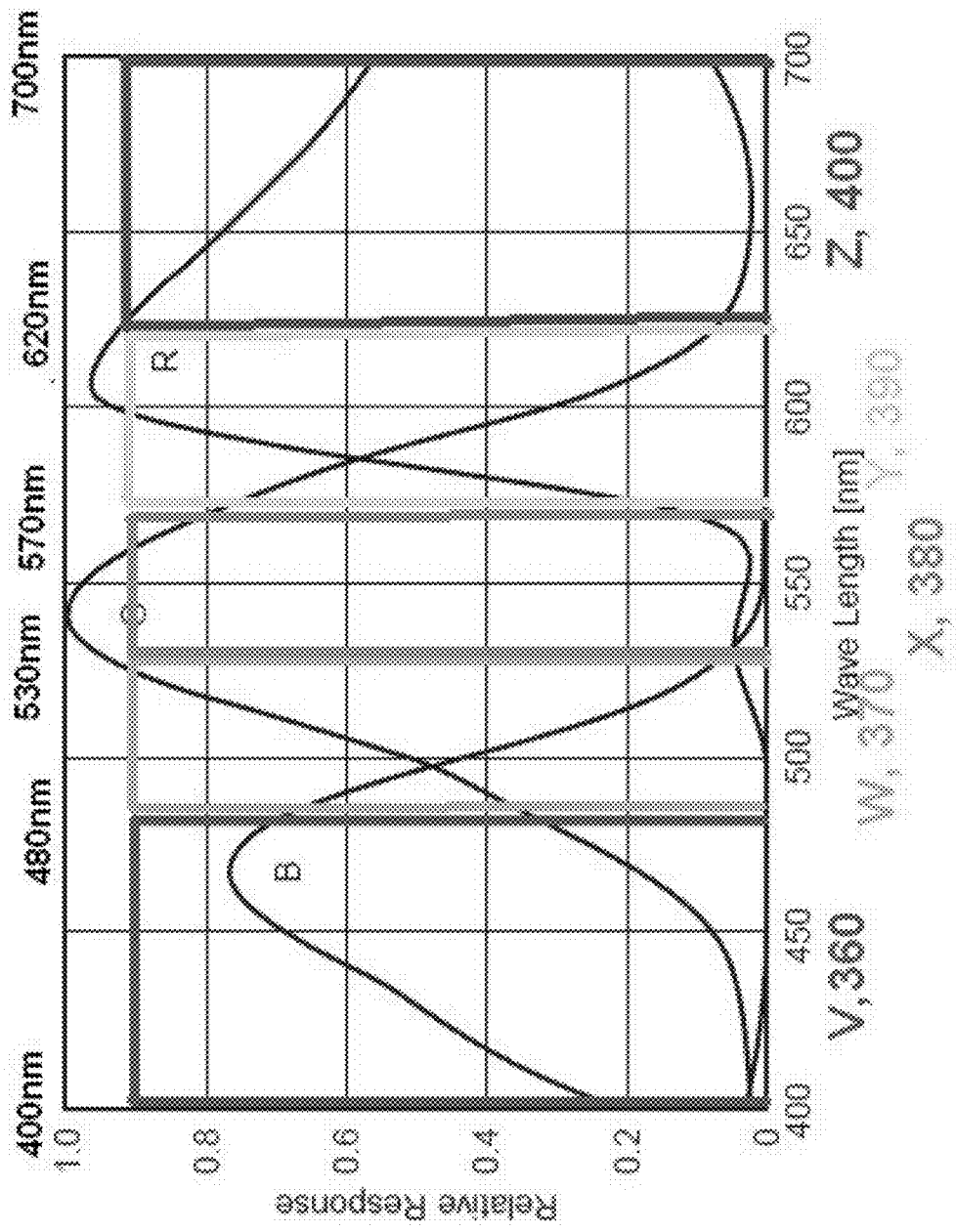
FIGS. 14-17 show the evolution from a five-band rectangular solution set to a linear algebra representation of the spectral data.

FIG. 14 shows a decent "5-rectangular band" Bayer-tuned Solution Set, with 80 nm, 50 nm, 40 nm, 50 nm and 80 nm bandwidths, respectively.

Figure 15:
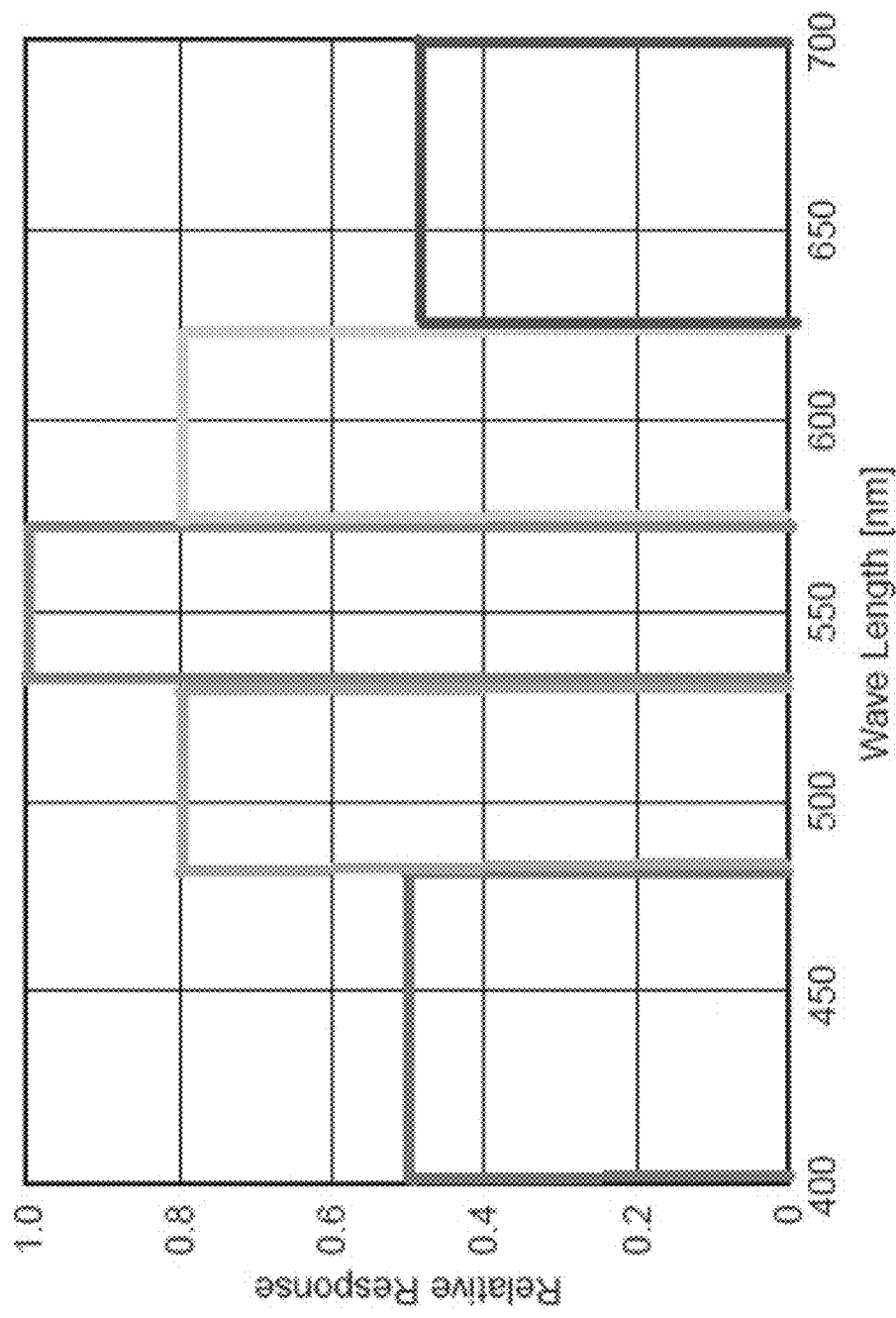

FIG. 15 shows a 5-band "Orthonormal" set of imaging spectroscopy bands, weighted for direct multiplication with the lighting-modified effective spectral response curves associated with B0-B3, G0-G3 and R0-R3.

Figure 16:
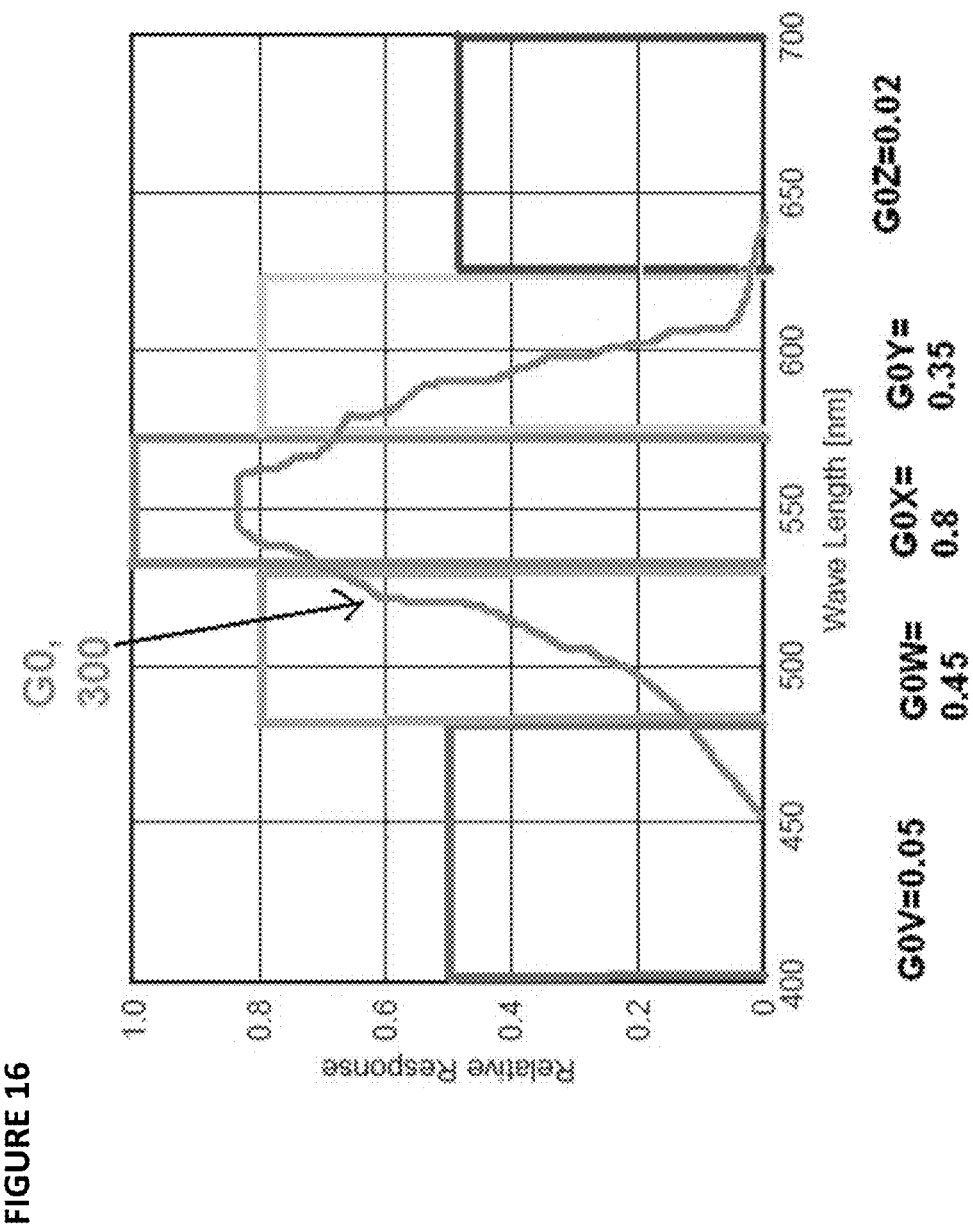

FIG. 16 shows largely empirical coupling value between effective spectral response G0 and all five chosen bands.

Figure 17:
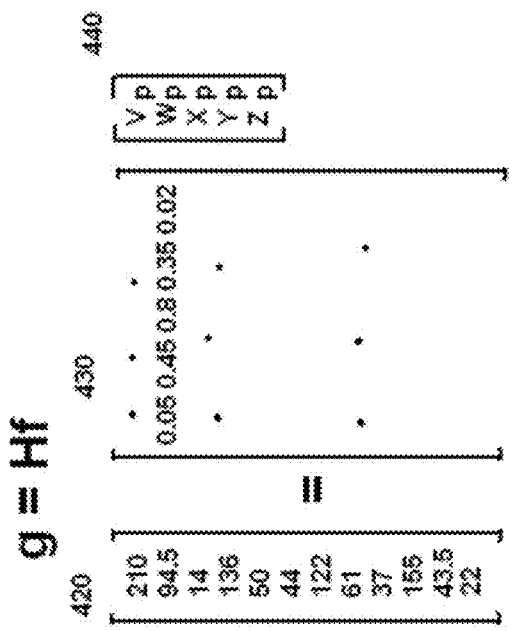
Figure 17:
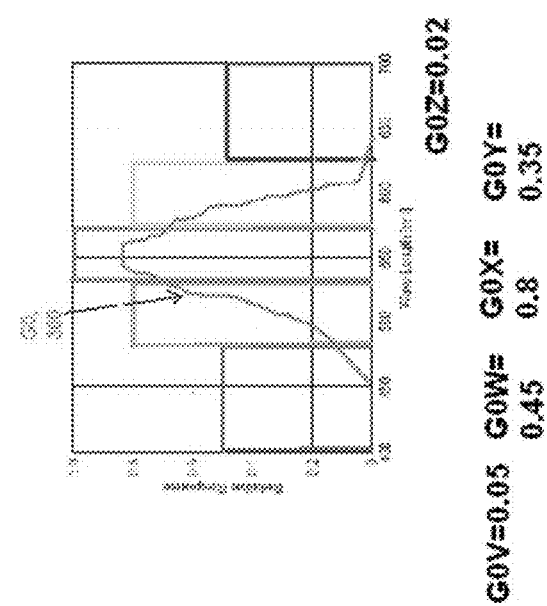

Referring to the left of FIG. 17, the "G0" row of the H matrix is calculated via simple area multiplications between an empirical light-source-modified sensor profiles and chosen solution bands (in the case V-Z). On the right, 'g' is the twelve pixel value vector (with the redundant green values averaged); H is the coupling matrix, and F is the sought solution. The G0 row vector is explicitly displayed, while the other 11 rows are implicitly filled-in by multiplying their effective response curves by the five orthonormal bands, as per FIG. 16. (The noted sub-script "p" indicates we are solving for our small apple patch.)

Figure 22:
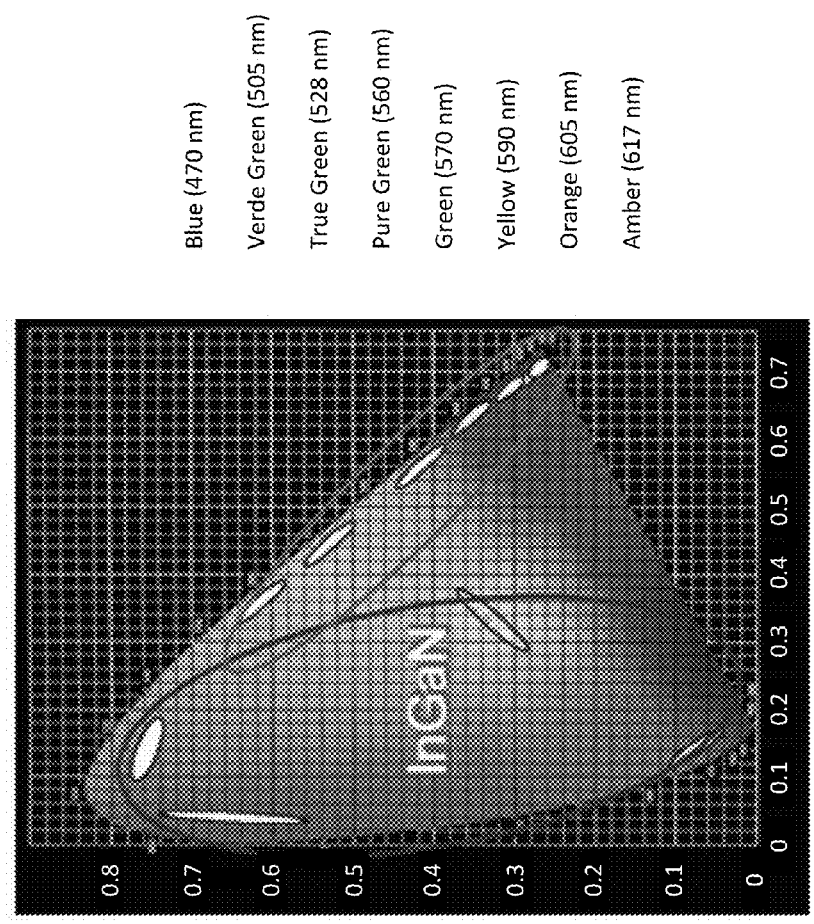

FIG. 22 shows various examples of LED spectral characteristics as plotted on the 1931 CIE spectral diagram.

Figure 24:
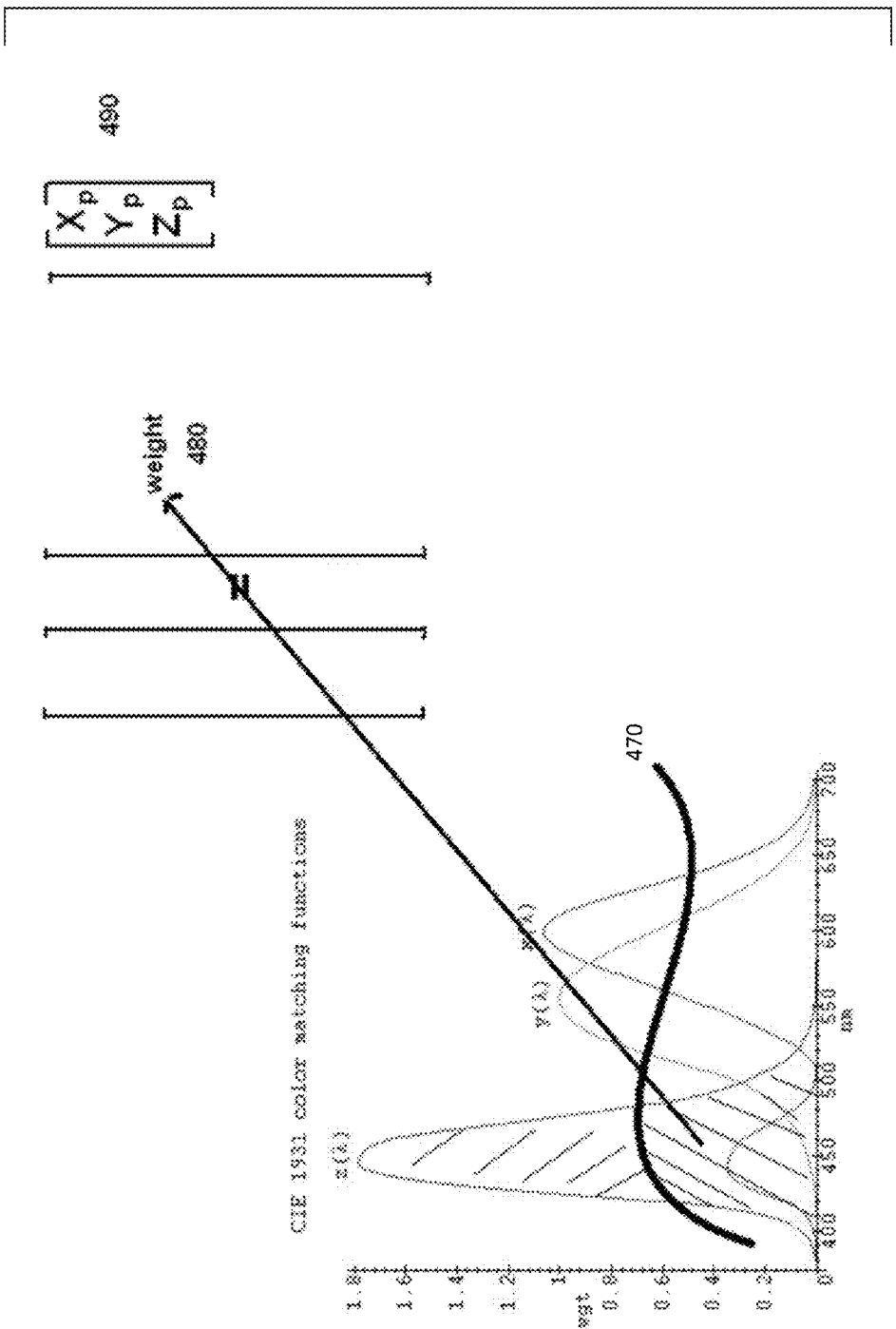
FIG. 24 details use of a CIE matrix to generate chromaticity coordinates.

FIG. 24 illustrates that solution bases functions can be many choices and not necessarily "orthogonal" or "orthonormal." Flash-modified pixel sensitivity functions also need not be Bayer/RGB/etc., as well. Here depicted is how explicit "CIE" solutions can be constructed from "arbitrary" flash-sensor profiles, where multiplication produces row values in our H matrix. Curve 470 shows an arbitrary flash-sensor profile to be multiplied by any chosen solution functions, here depicting "classic" 1931 CIE functions. (The subscript "p" again indicates we are solving for our small apple patch.)

Figure 25:
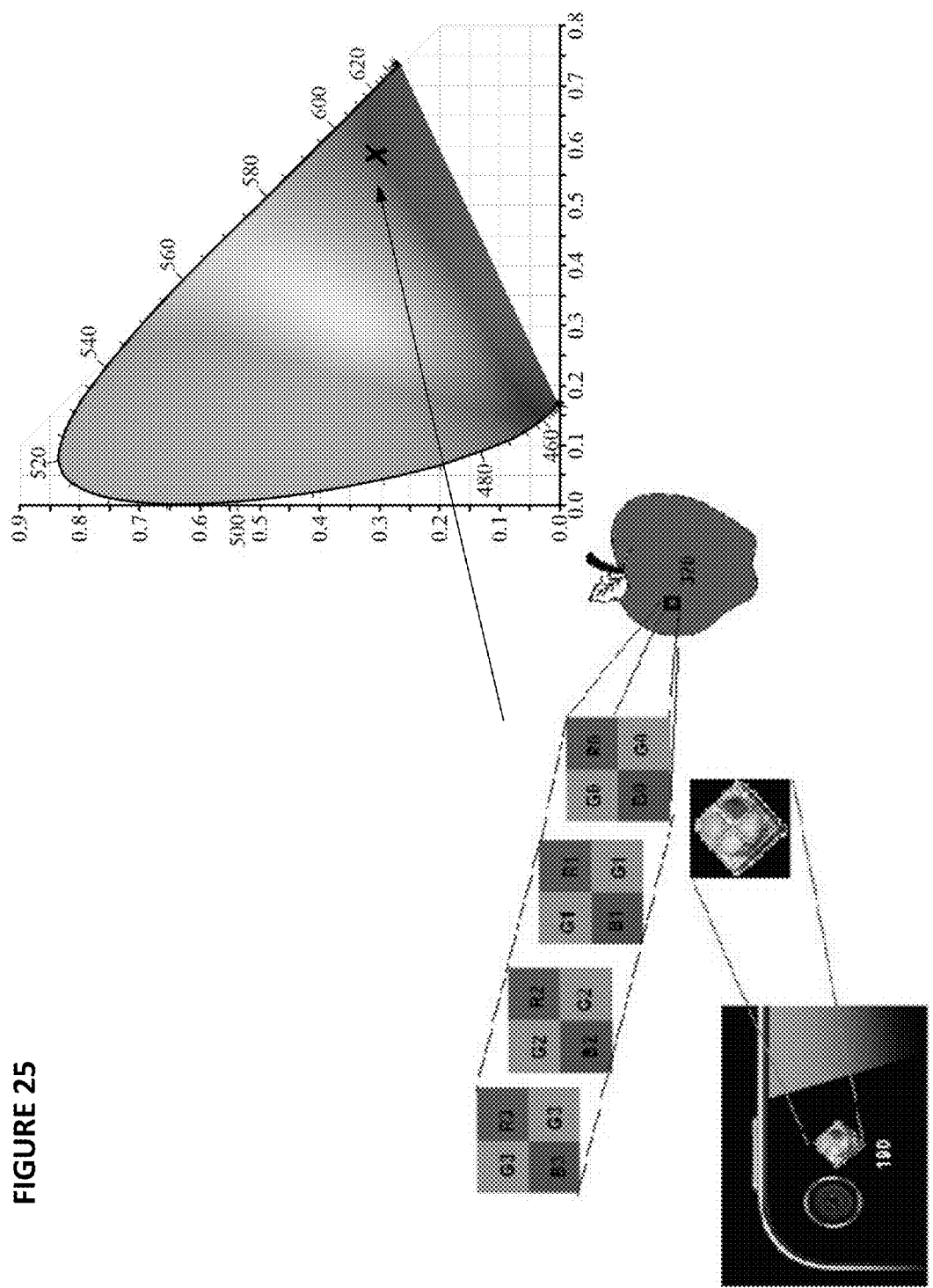
FIG. 25 shows how the present technology resolves an apple's color to particular coordinates on a chromaticity diagram.

FIG. 25 shows that "Direct Chromaticity Capture" becomes a natural consequence where (a) sensor profiles, (b) LED profiles, (c) "ambient light" treatment, and (d) the raw number of independent flashes . . . can all combine to approach near-full-gamut capture, and ever-tightening error bars on the capture.

Figure 26:
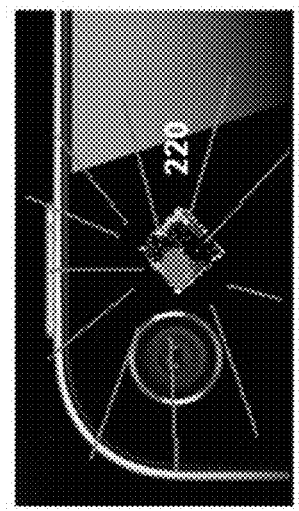
FIG. 26 delves further into ambient illumination combined with the LED illumination.
Figure 26:
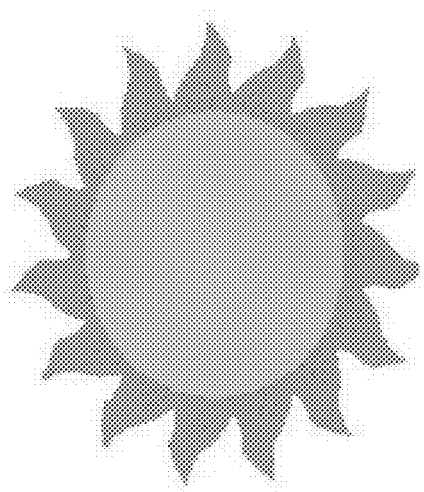

FIG. 26 contemplates that there are many ways to deal with "generally unknown" but often very typical kinds of ambient light additions to the pure flash, e.g.:

1) add an estimated ambient profile to ALL weight values in the H matrix;

2) strobe the flash so quickly, with synchronized strobing of the pixel exposure time, that ambient becomes negligible;

3) EXPLOIT IT! Use a pure ambient capture as part of the frame sequencing, giving N-5 in our 4-LED scenario;

4) Use common photographic measuring instrumentation to gauge the color temperature of ambient, then use this in H matrix correction factors;

5) Use "Flash-Frame Intensity Modulation" to cycle the intensity of any/all flashes, measuring the digital number modulation of the resulting pixel values against a "known" lumen modulation applied to a scene;

6) Etc. . . .

Figure 28:
FIG. 28 introduces use of the technology in food safety, item inspection, and anti-counterfeiting applications.

FIG. 28 illustrates some of the commercial/consumer applications of the present technology, beyond "richest color" photography, e.g., quick checks on freshness and quality of produce, for both proprietors and consumers alike (281); building and materials inspection (282); and counterfeit products "quick checks" (283).

Figure 31:
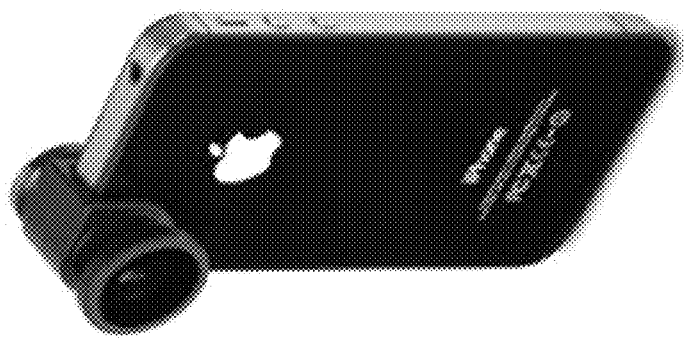
FIGS. 31 and 31A illustrate an implementation using a clip-on illumination accessory.

FIG. 31 illustrates how clip-on accessories are a viable short-cut to market as the long process of designing and integrating new LEDs directly into smart phones. (Depicted is a commercially available optic supplementation, but making this unit primarily a flash unit with either wired or wireless connection to the device is quite viable.)

Figure 32:
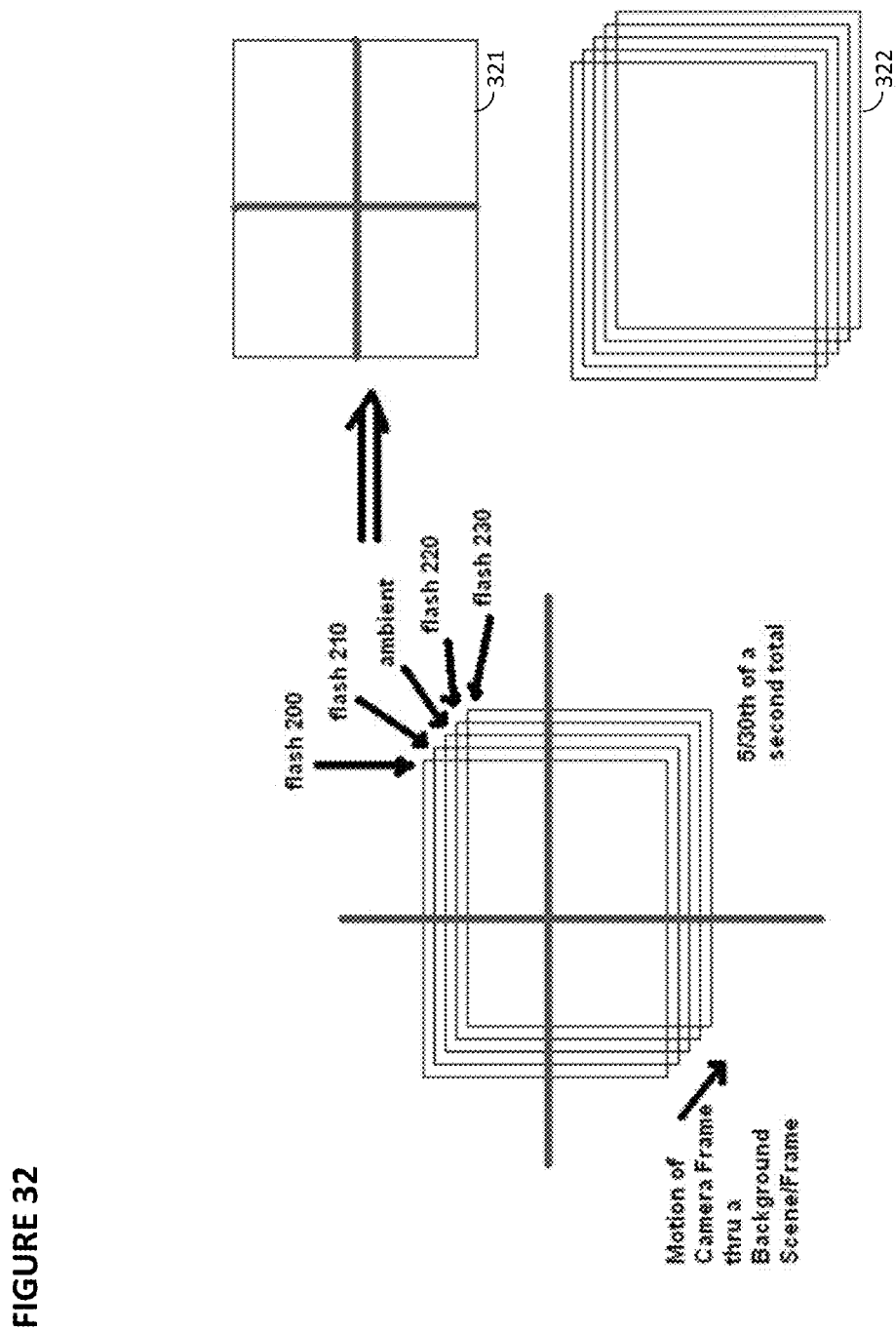
FIG. 32 addresses aspects of the technology concerning motion.

FIG. 32 illustrates an approach to deal with camera motion and motion photography (video; effectively motion deblurring in luminance, with the additional of chrominance "draping"). This involves dynamic linear luminance tracking (keying-in explicitly to time intervals between ⅕th and 1/10th of a second). At 321, "common" luminance-signal correlation can determine motion between frames, with subsequent re-projection of individual frames onto a shared frame—typically the middle frame. At 322, the same operation can be done on frames of a video; each individual frame can become a reference frame that the other four (in this example) re-project to.

Figure 35:
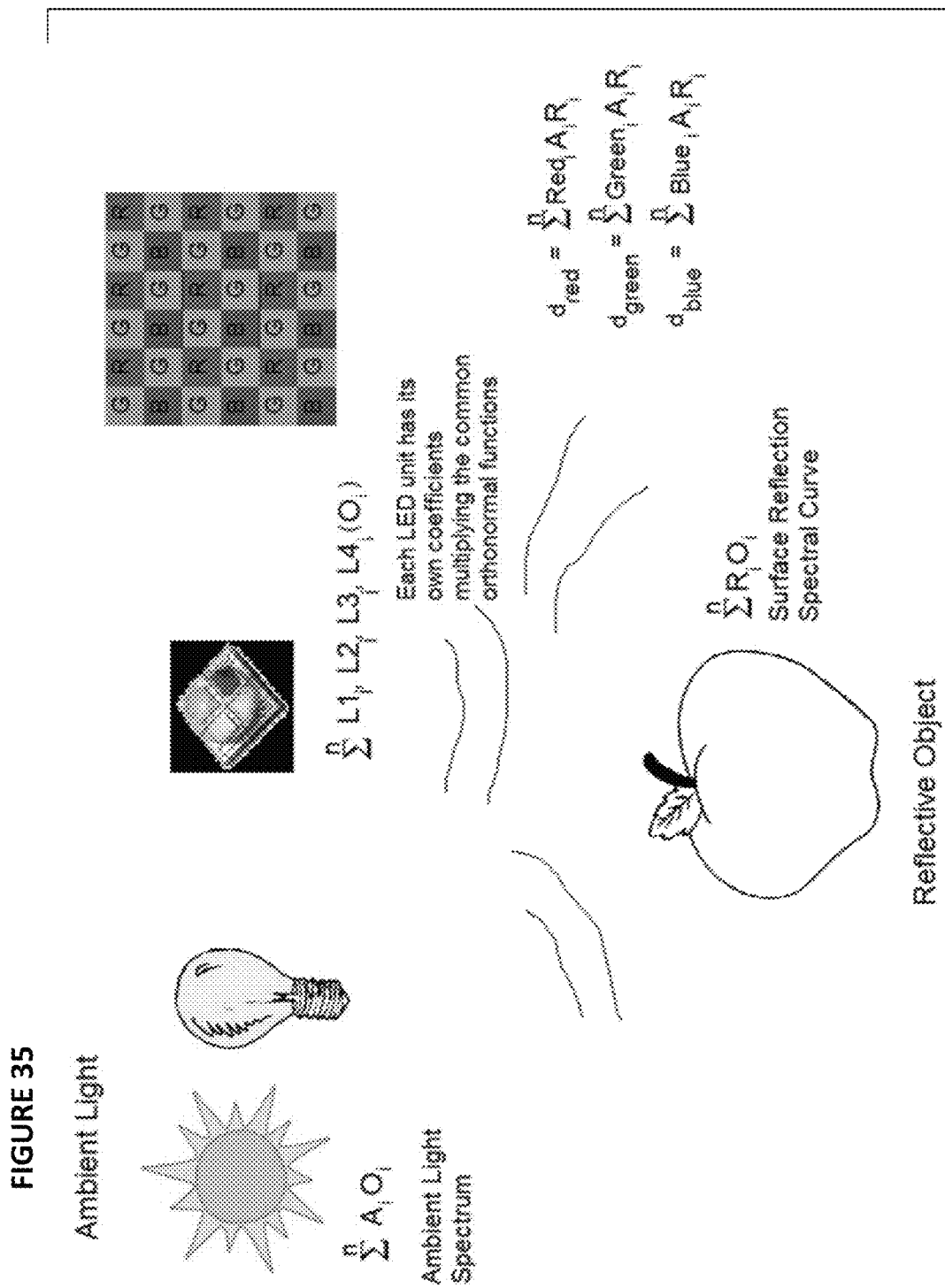

FIG. 35 posits that the LED units are not on, and a camera merely samples the ambient light, producing three datum per each cell of a Bayer sensor.

Figure 36:
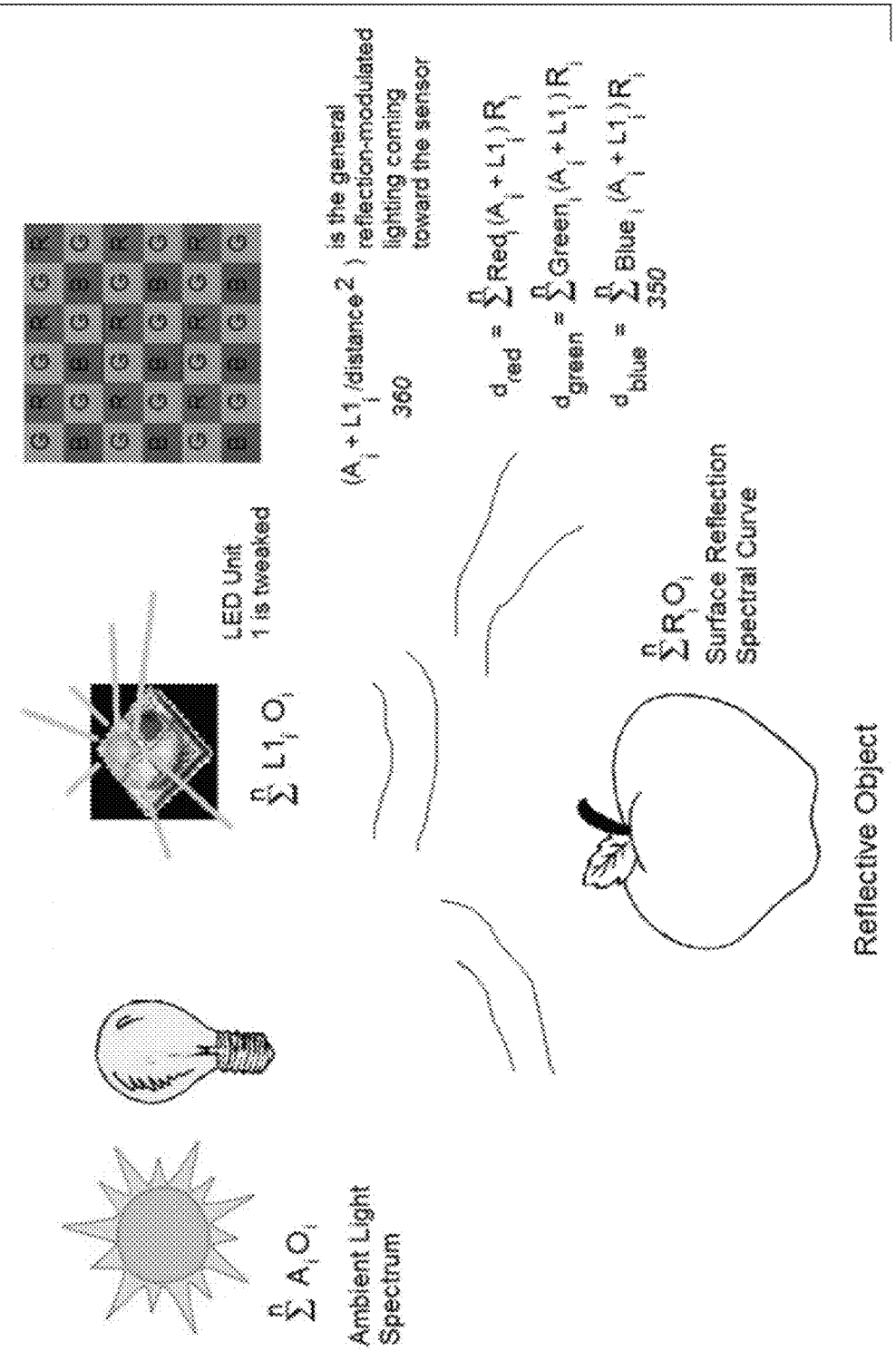

FIG. 36 is similar to FIG. 35, but here LED 1 is tweaked on and a distance-squared modified L1 term shows up in the collected samples from the Bayer sensor (distance-squared term not explicitly in equations).

FIG. 37 shows that individual LED tweaks can thus be isolated from ambient contributions. Here we see just one LED, number 1, and how we get three "g vector" measurement values that can roll up into matrix equations intending to solve the R coefficients (the unknowns). For surface "patches" involving thousands of pixels and allowing several LED tweak cycles, many otherwise noisy values can nevertheless produce superb patch spectral patch measurements.

DETAILED DESCRIPTION

FIG. 1 depicts how most modern cameras distinguish red apples from green apples.

An image of the upper-left-rearside 2012-era iPhone, 40, with camera aperture on the left, 50, and a small flash unit aperture on the right, 60, is shown, along with a simplified Bayer pattern representation of the camera's sensor, 70, depicted above the Iphone. With ten or fifteen minutes of discussion with Applicant's early grade school nieces and nephews, it does not take long to explain how the red apple, 20, lights up the little red-oriented sensors in the camera and the green apple, 30, tends to light up the green ones. [See FIG. 3, items 110 and 120 for explicit intuitive graphics for this only slightly oversimplified lesson]. But next the Koan sequence would lead to the simple question . . . hmmm, yungins, what if we were in a room with only red light in it, what would you see and what would the camera then see? Blue light? Maybe we'd even try it.

Anyhow, the simplest point is that lighting does matter and any specific 'normal' camera sensor will have measurably different behavior in its digitized signal outputs as a function of the spectral characteristics of the light used to illuminate some otherwise 'fixed' scene. The related simple point better made right away rather than later is that, as always, 'range' or distance of an object from a flash source is a fundamental issue to this technology, just like it is with all flash photography. Virtually all commercial flash photography has a practical range of a few meters at best, maybe 5 or 10 for special types of photography. The same types of ranges will apply to this technology, generally considered, and this disclosure will attempt to at least touch upon how 'spectral fidelity' will often decrease as a function of range.

Concluding the initial discussion of FIG. 1 then, we find two common lighting sources for the apples, the sun, 10, and perhaps our smart phone flash unit 60, perhaps individually or perhaps in combination. Obviously there are many other forms of 'ambient' lighting beyond the sun as well, and likewise, digital cameras in general have taken the technology of 'the flash unit' to quite remarkable levels of sophistication and expense.

Figure 2:
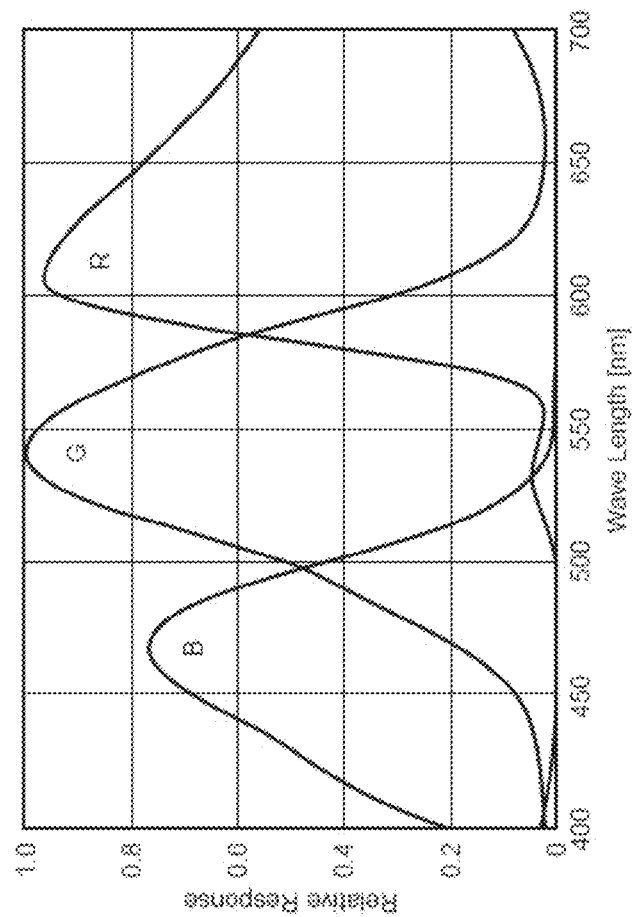
FIG. 2 presents a plot of three spectral detection profiles of an illustrative Bayer-pattern CMOS sensor.

FIG. 2 continues the 101-level summary of the technology by presenting a highly generic but also highly typical plot of the three spectral detection profiles, 80, of a Bayer-pattern CMOS sensor. The X-axis is the continuous rainbow blue (400 nanometer wavelength light) to red (700 nm). The Y-axis is labeled 'relative response' and for this summary can just mean how strongly light of a very specific wavelength can produce signals in a modern sensor (as manifested by digital values post A/D conversion). These curves are very familiar to designers of color cameras, sensor designers, etc. They are also generally familiar to more technically inclined photographers. Those familiar with such curves understand that there is great variability and subtlety in how and why these curves are the way they are, and manufacturers of cameras and sensors spend not inconsiderable time studying and re-designing how such curves manifest themselves. This technology adds new, potent variability into the fairly mature and 'stable' art of Bayer-pattern filtering in particular, as will be seen. Concluding the initial discussion of FIG. 2, however, it can be noted that by and large these filters have been and continue to be tuned in such a way that digital cameras can best 'match' or 'capture' natural colors as humans see such colors. Not surprisingly, these curves mimic what color scientists concisely refer to as the CIE color matching functions (and their many subtle variants).

FIG. 3 gets back to our red and green apples and a just-slightly oversimplified summary of how a camera can measure that a red apple is red and a green one green. We find a new green curve, pointed to by label 90, representing an idealized 'spectral reflectance' profile of a green apple, and likewise a red curve, pointed to by label 100, representing the same from a red apple. Color scientists understand that such curves never go to zero for any wavelengths and that the correspondence of the spectral shapes to the 'G' curve of a Bayer filter—and the a' curve—is pretty unlikely. But for this summary, that's just what these particular apples behave, how do you like them apples.

So, for intuition's sake, we can imagine close-ups of our Bayer-pattern sensor in a smart phone camera or a digital camera being 'lit up' in the green pixels, 110, when those pixels correspond to patches of the green apple, and likewise the red pixels 'light up,' 120, for patches of the sensor viewing the red apple. Imaging engineers, etc., all know this 'lighting up' is simply a nice correlation of innate spectral profile of an object with the spectral profile of a sensor, hence giving rise to much higher digital signal values in the pixel outputs. Indeed, this 'correlation' is generally accepted to be a multiplication of the quantified spectral light flux of a patch by the also-quantified spectral profile of the sensor. Said another way and described repeatedly in all books describing color science, this is an integral multiplication of two spectral curves, one weighted by light flux from an object, the other weighted by spectral quantum efficiency of a pixel, integrated from blue to red. The generally accepted result of such a multiplication are the well known digital number signal outputs from pixels, also taking into account commonly known issues of analog signal to digital count value factors as well. (all too much information for a summary, perhaps; after all . . . we're just showing that green apples tend to light up green-filtered pixels and red red!!).

FIG. 4 now introduces a highly idealized 'ambient' lighting source spectral curve, 130. The main point of this simple diagram is to highlight that all light sources will have a so-called spectral structure. Professional photographers learn this in diapers. A streetwise way to put it is: there ain't no such thing as white light.

The second point to FIG. 4 is that this generally unknown and generally ALWAYS DIFFERENT ambient white-ish illumination will produce slightly different output values to our R, G and B pixels of the Bayer (or other) types of filtered pixels. Again, this is all exceedingly well known to engineers and photographers, with the detailed point of FIG. 4 giving a first indication of how in this one example, the B pixels will be just a tad lower in their resultant digital values IF some object is lit with this particular type of illumination, RELATIVE TO, the G pixels. The effect in this displayed example might be on the order of 20% to 30% less signal showing up in the B pixels than might otherwise show up with purely 'white' signal or equal energy across the spectrum.

FIG. 5 continues the main line of summary from FIG. 4, now presenting an equally idealized but nevertheless instructive case of illumination here called 'slight green-ish mainly blue-ish,' 140, represented by a perfectly straight line from the upper left to the lower right of the coordinate background. The deepest point to this figure is that the spectral profile of light can be actively structured! (as every lighting engineer well knows). Depending on the type of lighting source, one's ability to structure illumination spectrally will often be highly constrained due to the raw physics of the light source one is using. For example, this perfect line from 400 nanometers full-on to 700 nanometers full-off is theoretically achievable (within, say, 5 to 10% in a 100% scale) using normal tungsten bulbs and some sequence of 5 or 10 well-chosen optical filters, but by and large it is not an easy matter to cudgel the spectrum of tungsten to do exactly what you want it to do, it has innate physics thank you very much and that's the palette we are given. Later sections will zoom in much more particularly on modern LEDs and the many choices of how to manipulate their 'raw physics' into, importantly, economical and practical spectral shapes.

But back to FIG. 5, we now find three new curves depicted labeled B,' 150, G,' 160 and R,' 170, representing the here-called 'lighting modified' effective spectral response functions of the Bayer pixels. The physics of the Bayer pixels will of course not change, but one can now 'know' how their actual response functions will behave IF one knows that a particular kind of spectral light will be illuminating an object/scene. The English-phrase way to put this might be: "OK Mr. Apple, I know that in purely white light my Bayer-pattern pixels will read out the signals and colors just like they ought to, but in this new light where I know the modification of the illumination profile, I also know that my raw pixel output signals will be more like the 'effective' profiles of 150, 160 and 170. So once again, FIG. 5 uses the common convention of putting a prime ' symbol on the three earlier curves B, G and R of FIG. 2."

FIG. 6 further continues this summary line by depicting our red apple, where if we don't tell our Bayer camera that we're using funky light to illuminate the apple, it will dutifully display the apple as yellow on a smart phone screen or some digital camera captured display! The yellow is mainly due to the notion that while the actual reflective spectrum of the apple has not changed from curve 100, FIG. 3, its 'coupling' or multiplicative integration with the new spectrally-shaped response curves G' and R' of FIG. 5 is now more even between the digital response of the G' channel and the R' channel. The R' channel goes down simply because the lighting has much less red in it. And the red apple spectral curve already had a little bit of coupling into the G channel in the first place (even though it is a 'red' apple), hence one might imagine that the resulting yellow will be a 'dark yellow' as a nit-picking matter. So, the point to FIG. 6, well known to virtually every professional photographer on the planet is: lighting makes a big difference to capturing 'true' color. FIG. 6 also foreshadows the important role of 'knowing' what the spectral characteristics of the illumination indeed are.

FIGS. 7 and 8 are probably as general a summary of certain aspects of the technology as one can muster. Plop a multiLED flash source in place of what in 2012 is either a single LED or a 'white' dual-LED, then synchronize its flashing to captured frames from the sensor, most often being a Bayer-sensor at least for smart phones.

As further disclosure and figures will elucidate, the individual properties (physics) of each LED within a singularly packaged multi-LED can be 'tuned' and/or optimized along a variety of design parameters, with 'cost' being the perennial Goliath parameter. The result, after processing to be discussed in detail, is that you've turned your smart phone or digital camera into a hyper-spectral imager. More importantly at a 'cultural' level, you've formed the groundwork for explicit 'true color' or what this disclosure call 'direct chromaticity capture' imaging. Arcane to many folks but not to color scientists, one now has the basis to have a normal Bayer/etc. camera directly produce 1931 chromaticity coordinate values, replete with highly testable error bars on those values. The physics of the LED choices, perhaps new choices on the details of the filter curves for the pixels themselves (see FIG. 2), all can combine for an analytic prescription for anticipated error bars on such pixel (or small patch of pixels) chromaticity output. One can immediately appreciate that once new sensors such as the announced Sony RGBW, and once LED spectral characteristics continue their inevitable advance, then direct chromaticity capture is simply a matter of engineering decreasing error bars on the values themselves, set against all the usual variables of distance from an object, glare, ambient light unknowns (to be discussed at length later), effective temperature of the flashing itself, motion, etc.

To the lay public, this technology will just be another chapter of 'weird stuff' that can happen when the flash is applied. Many camera and/or flash manufacturers have been playing games with flash for years and decades, so that's nothing new. 'Everybody knows' about pre-flashes, flashing flashes, etc. FIG. 8 just summarizes what is going on during a given 'flash session' if you will. Imagining that our CMOS sensor in the figure likes to expose and frame-out at 30 Hz, we get a glimpse of four sequential flashes, 200, 210, 220 and 230 of a current proto-example of a multi-LED, 190, FIG. 7. In this case, the four frames will be taken over a $2/15^{th}$'s of a second period. By 'proto-example,' above, it is meant that this particular 4-LED device manufactured by Edison corporation has not had the physics of it LED spectral emissions tuned or optimized for this particular technology, BUT, even with the innate spectral profiles of their current offerings (none is in figures because applicant has not located any), it is highly likely that even with this very specific 2012 model(s) of this device, many of the basic attributes of the technology should work.

FIG. 8 tries to generalize the 'four flash' scenario by using the '4*n+X' mathematics, where flash 200 gets X=0, 210 X=1, 220 X=2 and 230 X=3, thereby accommodating video sequences. A single photo, of course, can just be four flashes and be done. FIG. 8 also continues the somewhat idealized and generic summary line whereby the flash 'colors' are obviously different from each other as looked at by a human observer, but subsequent figures/disclosure will explore the spectral aspects of these flash sources. It should also be mentioned here that the smart phone itself (and iPhone in particular) is exemplified in the two figures, but the basic principles are quite applicable to traditional digital cameras, where the behind-the-scenes frame/flash synchronization will have slightly different physical realizations in digital cameras as opposed to smart phones. The latter are dripping with multi-functionality and wireless connectivity, and hence are tailor made for this technology. Digital cameras are more single-purpose typically and things such as frame/flash synchronization are already quite 'plumbed' as they say, but there will be more novelty involved in multi-frame synchronization surely.

Figure 9:
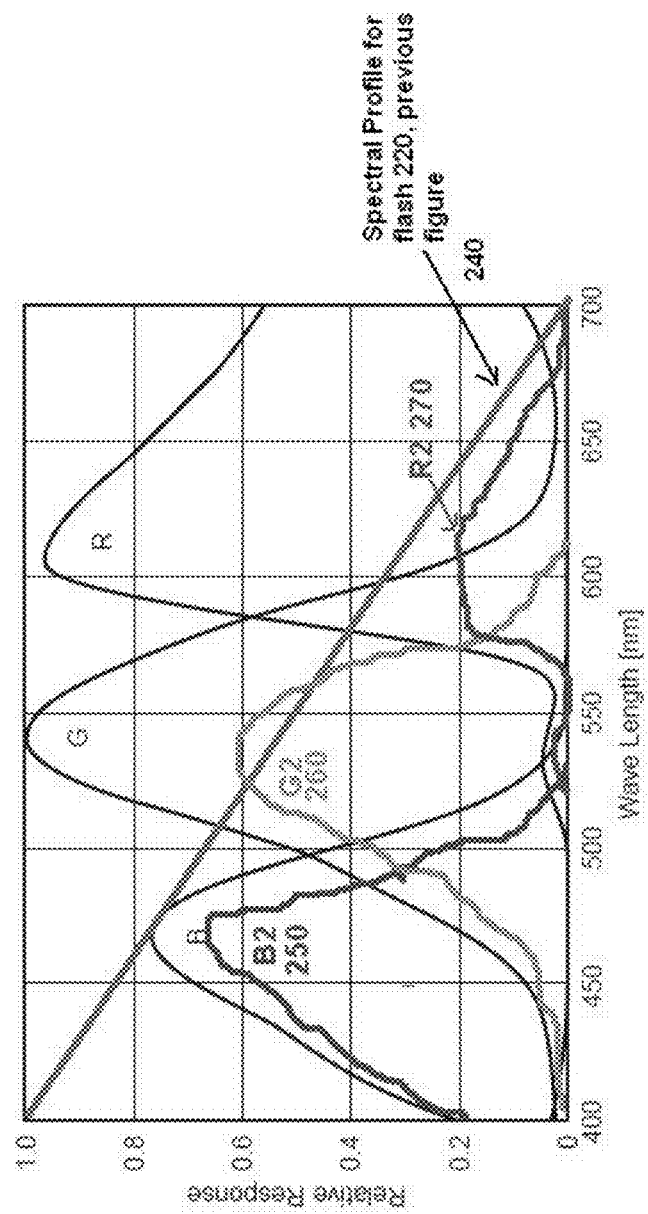
FIG. 9 is similar to FIG. 5, but incorporating insight from FIG. 8.

Continuing the summary line, FIG. 9 now blatantly copies FIG. 5 but re-enumerates some of the items to fit the example of FIG. 8. We can now fruitfully pretend that the particular purplish flash 220 of FIG. 8, derived from the left quadrant LED cell of multi-LED chip 190, FIG. 7, happens to spit out light with the spectral profile 240, our old friend the idealized straight line from FIG. 5. As later discussion will elucidate, both the physics of LEDs AND the desires of optimizing LEDs for this technology will probably dictate different results than these, BUT, this straight line still can nicely serve explaining how the technology works not matter what spectral profile one winds up with.

So FIG. 9 also presents another important but subtle change over FIG. 5, that is that we have now labeled the resultant effective spectral response profiles as B2, 250, G2, 260 and R2, 270. Why? These new numbers attached to B, G, and R represent the X=2 of FIG. 8, identifying which LED these curves correspond to.

Figure 10:
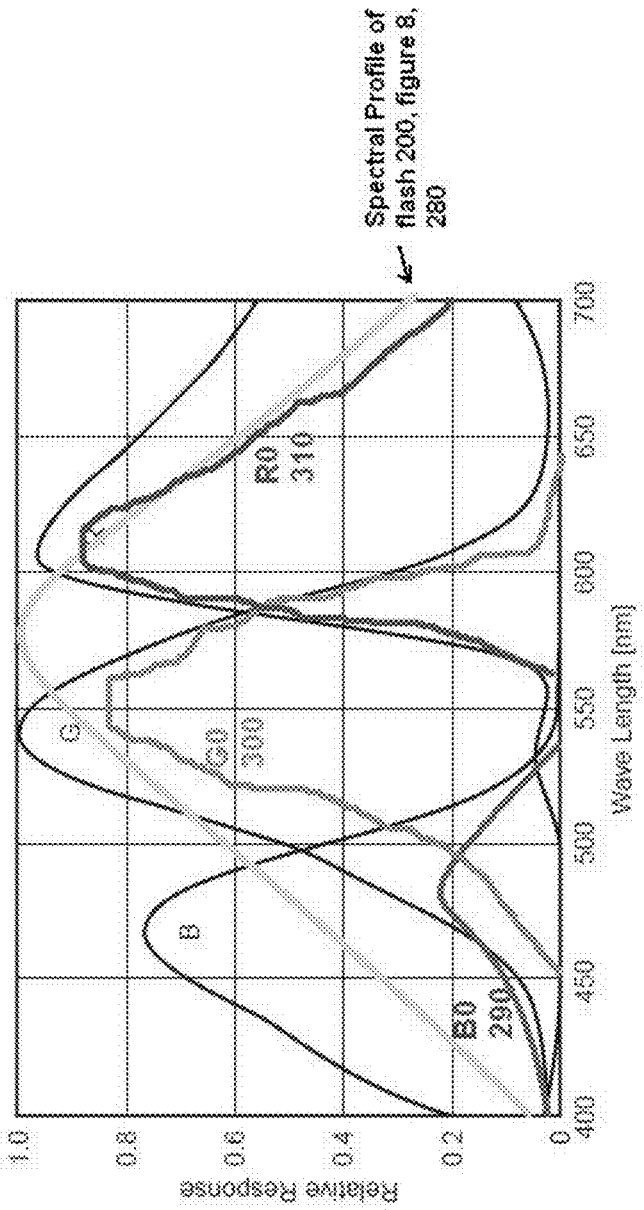
FIG. 10 shows another family of spectral curves.

FIG. 10 reiterates this basic point, now imagining that flash LED 200 might have a profile that looks like the curve 280 in the figure. We then can see the resultant B0 curve, 290, the G0 curve 300 and the R0 curve 310. FIGS. 9 and 10 suffice to make these matters clear, such that one can appreciate that flash units 210 and 230 of FIG. 8 both have their unique effective B1, G1, R1 and B3, G3, R3 respectively. All told, we have 12 unique effective response curves, bounding at least for this example the number of 'bands' we can measure at 12.

FIG. 11 competes with FIGS. 7 and 8 as being a general summary of certain aspects of the technology, only this time from the plumbing-side of the universe. One can imagine that we are in a pretty dark room taking a picture of this red apple, maybe 1 meter away from the apple. Our four flashes take $2/15^{th}$'s of a second to occur, the CMOS sensor grabs and stores four Bayer-frames of data. If we then zoom on one specific 'Bayer-cell' of green-red-blue-green, which happens to be 'focused' onto a tiny patch of the red apple 320 in the figure, we now can see the conceptual-yet-palpable explosion of that singular Bayer cell into a pseudo-3D array of 12 digital values (16 if we count the G's twice, but later we shall see that these are averaged in the simplest implementations). [Later, we will quite explicitly take away the condition 'in a dark room' and discuss the multifaceted and fascinating world of bringing normal ambient light back into the scenarios]. Rounding out the technical description of FIG. 11, then, we find the labels 330A, 330B, 330C and 330D applied to the 4 (or 4*n for video) frames captured under the four different LED lighting conditions. The figure attempts to be highly explicit that it is the same Bayer cell each time, just different in time and lighting.

FIG. 12 inherently asks the question: now what? So you get these 12 independent or 16 dependent numbers, what next?

FIG. 12 for fun fills in some hypothetical and quite realistic digital numbers into the 16 splayed "Bayer-cell sub-cells" as one might say. The question is explicitly asked in the figure labeled 350: how does this array of 16 8-bit values somehow translate into an estimate for the innate reflective spectral profile, 340, of the apple patch 320?? The depicted curve 340 is explicitly different from the red apple's curve, 100, FIG. 3, precisely to illustrate that we don't yet know what it is and we must find some way to estimate it given only the 16 digital values.

A very, very brief side trip into the limitless world of functional estimation cannot be avoided in this summary line, largely depicted in FIG. 13. This is a laughingly tippy-tip summary of how one can 'parameterize and discretize' otherwise continuous functions, knowing that there are trade-offs in the process. The benefit of the process is as simple as it comes: you can estimate functions using a countable set of numbers. The trick then just becomes turning one set of numbers, our acquired 16 digital values of FIG. 12, into a new set of numbers which multiply some chosen set of these so-called bases-functions, hopefully producing a function which gets as close as possible to the 'unknown curve' 340, upper right of FIG. 13. The reason applicant felt it was imperative to take this side trip into an area that many mathematicians take for granted is that some of the most profound engineering challenges of practicing this technology will be contained in the subtleties of choosing proper bases functions and specifically in matching innate physics of LEDs and pixel-filtering to such bases functions as the 1931 CIE curves. Applicant has not yet performed, yet full expects to during broader implementations of this technology, very detailed looks at the performance benefits versus implementation cost trade-offs between, for example, using discrete versus continuous bases functions as but one example. The figure shows examples of both accordingly, dusting off an old favorite named Chebyshev Polynomials, a mathematical gem with an appropriately obscure and evocative name.

FIG. 14, however, evokes the old phrase measure it with a micrometer, mark it with a chalk and chop it with an axe! But this axe is not all that coarse and indeed, it may for many applications wind up being a highly useful and practical approach to basic hyper-spectral imaging and the vast world image processing that entails.

FIG. 14 depicts a 'custom' set of 5 basis functions intended to be a first cut at what might nicely work for both the physics/psychology of human vision as well as the physical practicalities of CMOS/CCD sensor response profiles, LED spectra, etc. It is an explicit compromise between a purely hyper-spectral system that might posit 5 equal 60 nanometer bands from 400 to 700, and one which takes into account that Bayer-profiles already bias raw information content of sensor data into the 'photopic' region of the spectrum, i.e., the region tuned to human vision. So why not let's tune our 'simplest' bases functions (aka 'bands') to this region as well. We will later discuss the very important bases-function choice of the smooth CIE curves. FIG. 14 thus continues the important summary line of the technology, emphasizing how the basics work and leaving important variants for their own sections.

FIG. 14 presents the newly minted bands V, W, X, Y and Z, how original! V just happens to be violet-ish, Y yellow-ish, but there is no intent here to sanctify these bands nor tread on the many existing bands of color science and astronomy. The intuitive rationales to these functions, certainly subject to empirical tuning once real Bayer-sensors and real LEDs are in the picture, include: a) symmetry; b) an nice spread around the 1931 CIE chromaticity diagram; c) a coarse 'coupling balancing' between the typical R, G and B curves of a Bayer sensor; and d) a very nice 80/50/40 ratio of the bandwidths, which introduces the next FIG. 15.

FIG. 15 adjusts these bases functions to become so-called orthonormal, a fancy way of just saying the areas under their curves are equal (and equal to '1' if you really want to nit-pick the y-axis scaling). So what is the deal with these five box functions? The deal is that we are going to try to estimate object spectral profiles (over each and every Bayer-call of four pixels) using these boxes as our curve-fitters, that's the deal. FIGS. 16 and 17 will take us through the mechanics.

Starting first with FIG. 17, at the highest level we are just going to create a very classic 'linear transformation' between our 16-valued acquired vector and our newly minted VWXYZ vector. Give me a 16-valued 1-D array of numbers, I'll give you back a 5 valued array, try that with dollars and people, a profit of 11 numbers each transaction, not bad. The traditional form of this transformation, especially when you have a situation where functions behave nice and linear just like spectral profile multiplication does, is the matrix equation form, depicted as g=Hf.

We will return to FIG. 17 but let's look first to the very elemental operation required to even talk about a 'transformation.' What exactly is being transformed. FIG. 16 tries to answer this simple question: Any given response function (of our 12, with G0 singled out, 300, in the figure) will 'linearly couple' or 'transform' or 'light up' or 'choose your English word' into our chosen bases group, here using FIG. 15's VWXYZ. This is just what it looks like, an area based integration of the multiplication of one curve by the other, sequenced across all five VWXYZ bands. To make this a bit more tangible, label 410 is by 5 new entities below the graphic, given the names G0V, G0W, G0X, G0Y and G0Z. These are the so-called coupling coefficients between our chosen bases functions and this particular effective response curve. Some crude estimate numbers are thrown in there both for fun as well as roughly showing that they correspond to the areas whereby G0 spreads its energy into the various buckets, the numbers being typical integrations.

So FIG. 17 is a descriptive-text-rich diagram as applicant believes some figures ought to be largely self-contained in their description, not requiring text such as this. But, forcing an overview discussion here, we find our matrix formulation now partially filled out with bona fide numbers, hooray. We see twelve numbers in the g vector, down from 16 because we chose to average our pseudo-dependent G values in each Bayer-cell. This is the acquired data and it will change each image to the next. We then can see a shrunken version of FIG. 16, here in FIG. 17 now explicitly calculating but one of our 12 rows of the H matrix, 430. It is implied that this operation will be done on all twelve rows, using each of the unique individual response functions run through the FIG. 16 washing machine.

Then we find the f vector, 440, now populated with V, W, X, Y and Z subscripted by a 'p,' 450, because will be performing this transformation of 12 numbers into 5 numbers for every Bayer cell associated with all 'patches' that make up a full image.

The good news is that this highly explicit matrix equation is not required in the implementation of this technology, there are very well known ways to create inverse matrices which just vector process 12-valued vectors into 5-valued vectors. The steps required in creating these inverse matrices can be as involved as the whole functional estimation world of FIG. 13, replete with 'regularization' of poorly ranked matrices and the like, but these topics are not for summaries. The even better news is that the summary section of this disclosure now concludes and the remainder of this disclosure will discuss various nuances and alternatives to realizing this technology, with the 800-pound Gorilla being the use of CIE bases functions instead of hyper-spectral-ish bases functions.

Optimization

Figure 18:
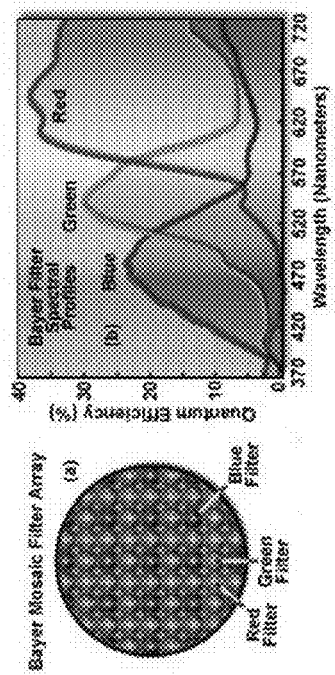
FIG. 18 introduces some of the considerations from a sensor side of the system.
Figure 18:
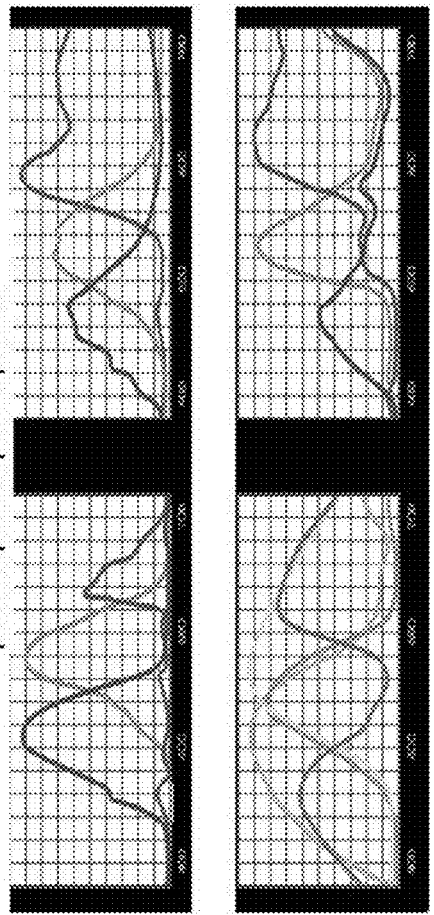
Figure 19:
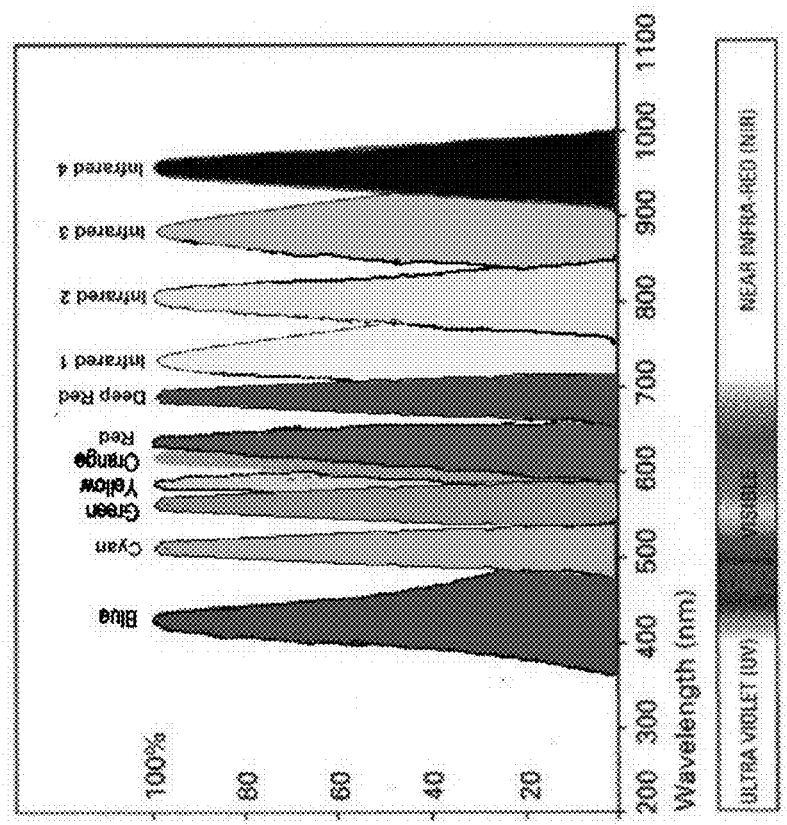
FIGS. 19-22 delve into considerations concerning the illumination LEDs.

FIG. 18 conveys in a single picture that there is all manner of flexibility on the sensor-side of this technology in terms of innate pixel spectral sensitivity profiles. Ever since Bryce Bayer of Kodak develop the single-chip color solution, no end of refinement went into finding better and more cost effective solutions ultimately determining the productized forms of the spectral curves. Also depicted in FIG. 18 are digital camera spectral curves, 460. One even has four different spectral curves, all the better, where adding a fourth inherent sensor band merely increases the effective 'independent' number of response profiles. Sony's rather new 'RGBW' sensor lay-out, previously mentioned, is simply heading in directions that this technology can exploit.

Figure 20:
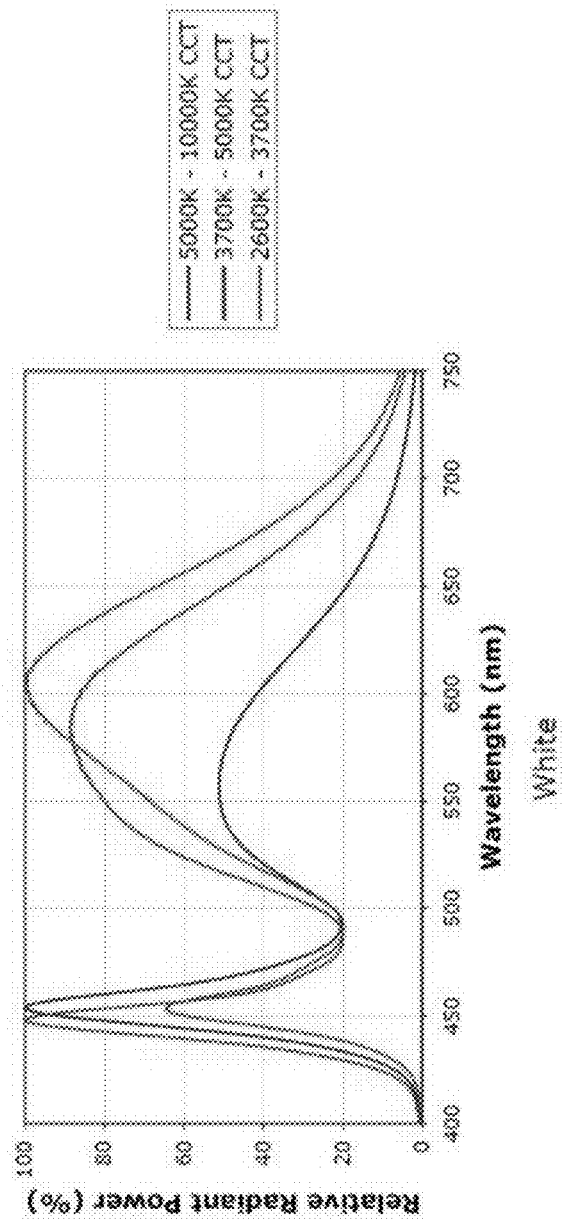
Figure 21:
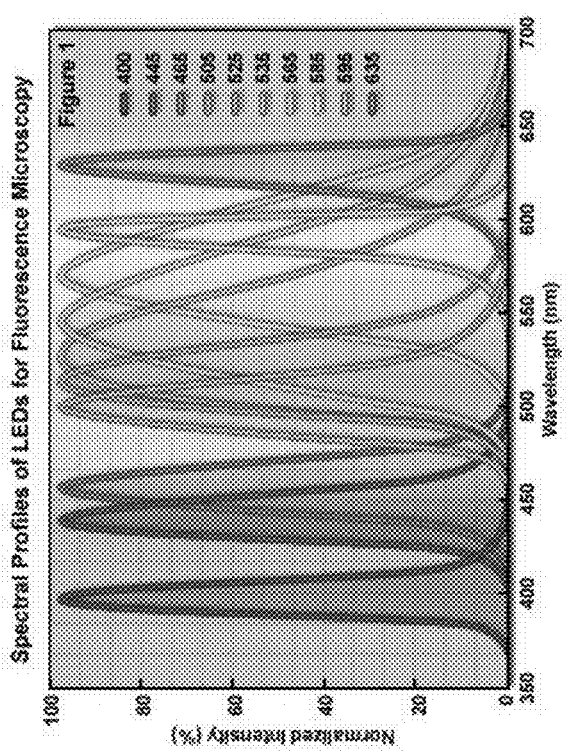

FIGS. 19-22 all collectively attempt to convey the very rich 'design space' represented on the LED-side of this technology. Depicted throughout these figures are various copied diagrams from not only different manufacturers but different industries as well, with FIG. 21 explicitly lifted from a fluorescence microscopy work. FIG. 20 displays a fairly typical spectrum of a 'white' LED, where this is actually a family of curves showing that slightly different spectra can be achieved based on a variety of design-scope decisions made on materials, drive electronics and even physical temperature if applicable. It is fully anticipated by applicant that this technology will add another log to the fire well burning already in the LED industry, a fire which is always pushing for new spectral properties all within generic economic constraints.

FIG. 22 also serves the purpose of a more formal introduction of the heretofore much-touched-upon 1931 CIE chromaticity diagram. A full introduction to this rich diagram and its 7 decades of development is radically beyond the scope of this disclosure, and we shall be content here to simply say that it remains a bedrock of color science.

Figure 23:
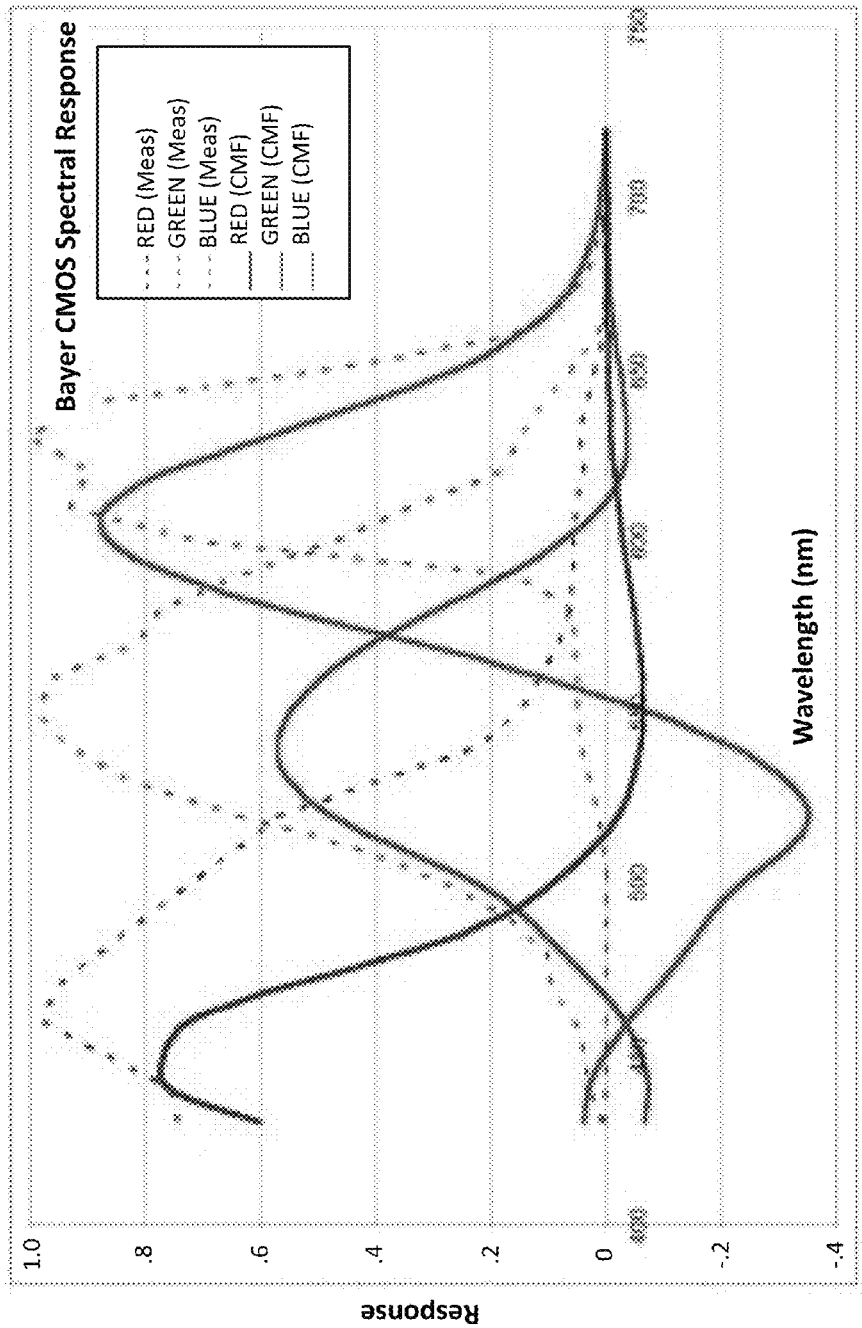
FIG. 23 illustrates a relationship between Bayer filters and orthogonal color matching functions.

This disclosure will discuss primarily using the raw x, y and z 1931 color matching functions (FIG. 24) but the reader should understand that there are many transformed variants of these functions, including orthogonalized versions depicted in FIG. 23. All of the subtle variations have their rationales and areas of strength, so by choosing the classic 1931 functions this disclosure once again has explication trump the black hole of optimization and perfection, an activity best left to commercial and proprietary efforts that drive one competitor to have a winningly-distinguished product over another.

FIG. 23 serves as a form of historic reference on how the design of Bayer-filters for pixels has been related to orthogonal color matching functions. The intuitive trick for Bayer-sensor designers of the past has been to 'generally match up' the filter-based responses (which includes silicon sensitivity functions) to the classic human vision color matching functions. With a rough fit thus obtained, a designer could then perform highly sophisticated modeling and testing of how well a given color camera would perform relative to its ability to 'nail' chromaticity coordinates of objects, AS a function of the innate spectrum of those objects and the lighting conditions—comparing and plotting generally error ovals similar in visual kind (but not substance) to the ovals in FIG. 22. In short and perhaps a bit too oversimplified, once a designer find that physics-based witches' brew of filter goop, they were pretty much stuck with the chromaticity-error behavior of the devices. One small objection to Bayer-pattern CMOS over the years, relative to the wider flexibility inherent in 3-chip color cameras for example, has been this limitation to goop characteristics irreverently described. Word on the street in 2012 is that more and more manufacturers have gotten the goop significantly better where innate capabilities of the goop matches the functions better and better. In any event, the aspects of this technology dictate that getting the goop close to some of these curves is all well and fine (helpful, yes), but when combining this with sequential structured-spectral LED lighting, once now has a whole new dimension to tune in to analytic chromaticity matching. The upshot of this is that a sensor-LED combination of design principles can lead toward an unequivocal engineering pathway toward precision chromaticity recording, replete with all-possible-object-spectrum variation plots within the CIE chromaticity diagram itself. In other words, one can model 'all possible reflection-spectrum' objects that have a specific chromaticity, then directly see how those objects will be measured—chromaticity-wise—by a camera with Multi-LED flash as per this technology. Error-bars, or error ovals, will still be in full play but adding the LED physics to the party brings in the steroids.

FIG. 24 then explicitly introduces the classic 1931 x, y and z curves taught to color scientists in their very first lectures as students. A deliberately generic LED-sensor combo profile is included, labeled 470. Whatever set of pixel profiles and whatever set of LED profiles produce whatever larger set of combined profiles, they all multiply by these three classic curves giving rise to what the figure calls a 'weight' in the matrix, 480, but a dozen different scientists and mathematicians will give it two dozen different terms. The bottom line is that it is a single numeric value placed into the H matrix, with this particular CIE matrix having only 3 columns corresponding to the three classic curves. To the right, then, is the unknown f vector being solved for, labeled 490. Same deal as before then: any given 'patch' corresponding to a Bayer cell, and RGBW cell (maybe even a 9 by 9 cell with 81 different filters!) will give rise to this inherent matrix, inverse matrices (vector processing coefficients) will be generated, then out will pop direct CIE color matching coefficients which then . . . voila . . . skipping the mathematical step of turning Xp, Yp and Zp into a 'chromaticity coordinate' . . . turns into an X, 500, on FIG. 25.

FIG. 25 also wants to compete with FIG. 11, which itself wants to compete with FIGS. 7 and 8, as being a high level summary of aspects of the technology. But FIG. 25 won't win because the 1931 CIE diagram is pretty arcane and contained to the color science community and its immediate brethren, AND, hyper-spectral imaging in general goes well beyond matters dealing with only human vision. So, we can grant FIG. 25 a claim to summarizing one of the most intriguing consequences of the technology at least.

FIG. 26 also must play the role that other figures already have played of being a pointer to rich and varied proprietary activity as opposed to any kind of grand description or summary of such. The subject is how one deals with ambient light in both a rigorous as well as a practical way. The answer is gazillions.

The figure unabashedly presents a humble text list of five particular 'things' designers and engineers can do, with a not-possible-to-be-more-explicit suggestion to use common ingenuity and best engineering practices to develop specific approaches and distinguish your offerings accordingly. This is not a 'punt' of this whole topic, it is an act of humility whilst facing design and implementation issues that hundreds and thousands of very gifted people in the past have grappled with, and inevitably as many more will do so in the future. This is where the allusions of religious fervor were previously invoked.

So, the list in FIG. 26 starts with a very simple approach which certainly should do for most 'normal consumer' photography, but surely even more sophisticated things will be done even in this application. To wit: design in a little button (or some buried user-choice menu item) a simple switch that has a little sun, a light bulb, and maybe a moon or something).

Better yet, don't even make the user do anything, just figure things out from the captured image data itself using many known image processing techniques. But, the core approach is to estimate the ambient lighting characteristics, especially its general brightness level relative to the flash brightnesses, and just add this estimate to the H matrix row values outright. This exercise is left to the reader and is well known to those practiced in image processing where 'ambient effects' need to be dealt with one way or another.

Item 2 in FIG. 26 presumes a pretty bright LED source and envisions its pulsing on a fairly short period along with an equally short exposure time for the pixels. This inherently will bring down the ambient levels of light simply by reducing the active exposure time OF that ambient light. For example, 1 millisecond exposures every $\frac{1}{30}^{th}$ of a second will clearly have 33 times less ambient light content than 33 millisecond exposures!

Item 3 can be done in combo with other. It is the notion that if you can't beat 'em join em.' By all means take an image with just ambient light! Simple. You can even use this as an estimator for item 1. You can also then use it in your matrix equations if you have sufficient confidence in the ambient light's general spectral profile. If the application is 'decent color photographs,' a little bit of error is not always a bad thing, go ask anyone who plays with color in Photoshop.

Item 4 is a kind of cheat but very possible as well. There are so many photography gizmos out there, use 'em. Light meters and auto-light gauges and sunshine sensors (GPS coordinates even) . . . all of these can provide useful information to any form of data correction, compensation, etc.

Finally, item 5 is a bit of an odd one but quite workable for the very serious photographer (or hyper-spectral imaging practitioner). One might not know the relatively stable background 'lumens' value of the ambient light, maybe it is say 50 lumens for some given patch of the apple, but one CAN flash that patch with 30 lumens of this flash, then 40, then 50, then 60, knowing that you are pumping in 10 lumen increments, then differences on your sensor data should correspond to the 'known differences' that you are pumping onto the scene. Patches of objects should also respond linearly to these increments as well as absolutes in brightness, so hey, for you precision measurement types out there that want and/or need pretty analytic approaches to fine-scale spectral measurements with as much of ambient background removed as possible, this might be your ticket.

Sample Applications

It might turn out that the main application of this technology will be dominated by simply being applied to the many decades of advance in color imaging, who knows. But this section and a few diagrams tree-top discuss some other applications.

Figure 27:
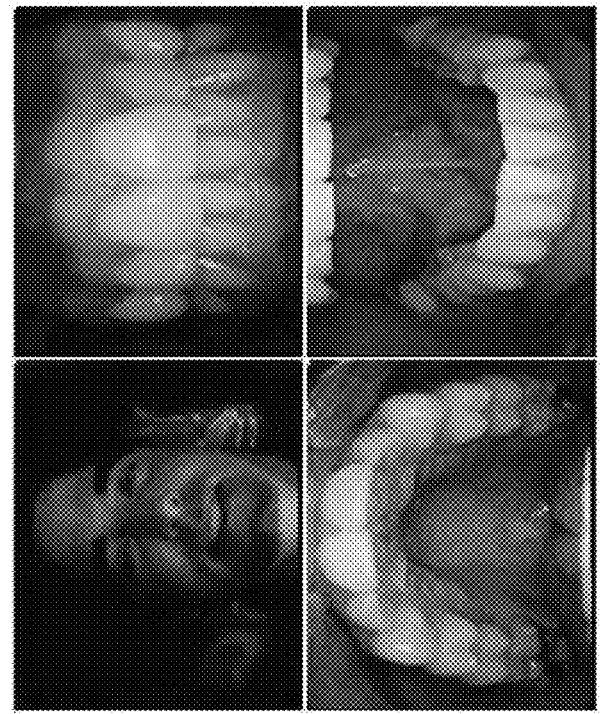
FIG. 27 illustrates uses of the technology in medical applications.
Figure 27:
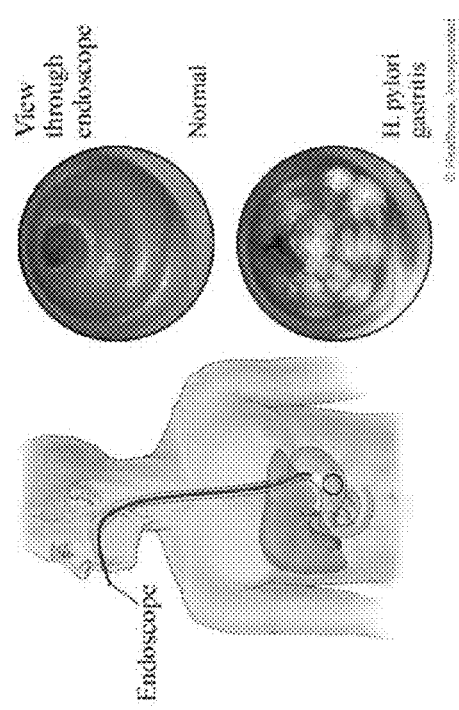

FIG. 27 illustrates two of the starker and clear potential medical applications of this technology. In both of these cases and many other medical situations where 'color cameras' are used as a core part of the practicing of some given medical art—hello—hyper-spectral analysis of pixels will virtually always trump simple human visual color scrutiny in terms of raw diagnosis capabilities. Is there hyper-spectral tuned diagnostic database out there in the world? No, not much yet to applicants' knowledge, but boy there ought to be. Normal versus abnormal biological clusters in the colon, esophagus and stomach will all naturally create more of a 'signature' in 4 bands or five bands or more, than they will in human-visual-system tuned RGB. Clearly, Doctors will rely heavily on human color perception as well, but that is not the point—fine, keep doing normal color viewing/analysis like ya do, but bring a whole new view to the situation. Doctors have long proven that any new tool of diagnosis will be eventually welcomed and put into practice especially if the costs keep coming down. FIG. 27 also has dental imaging there for grins. Applicant would be afraid to use this technology on his own mouth for fear that I want to go seek professional cleaning far more often than he currently does!

FIG. 28 then attempts to do a modicum of justice to an otherwise bewildering array of potential applications both on the purely 5+band hyper-spectral imaging side as well as the 'true color imaging' side. The beyond obvious application is simple food/produce quick quality control, both vendor-side and consumer-side. Vendors may freak out thinking that all their customers might some day be inspecting making their fruit purchases with their smart phones rather than the squeeze of some grimy fingers, but hang on, maybe that's a good thing? And surely the cat and mouse game of true quality versus presented quality would find new chapters of sophistication . . . but the point remains, this technology has the potential to play here. Likewise inspections, counterfeit 'suspicions' if not outright 'proof,' all possible. The figure is embarrassingly high level in its attempt to summarize the applications, with surely ten years hence answering the question better.

Figure 29:
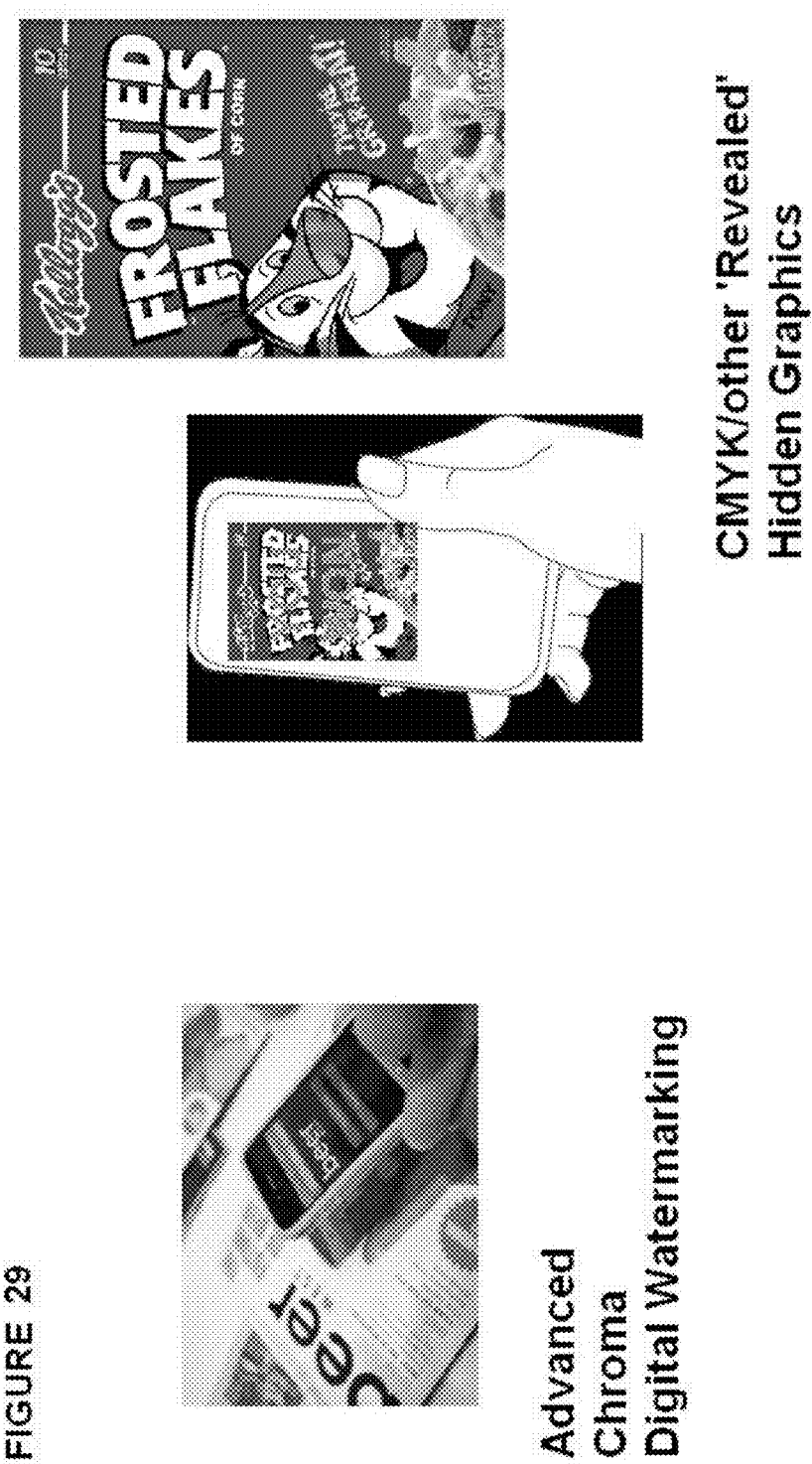
FIG. 29 illustrates use of the technology in digital watermarking and related applications.

FIG. 29 then alludes to a slightly more niche world surrounding identity, printed graphics, packaging, etc. Digital watermarking and 'fingerprinting' are both well-known methods for identifying objects for a range of applications, and the printing industry has always found various interesting technical gimmicks to spruce up its fare (such as color-based stereo printing where colored glasses can reveal 3-D forms, as but one simple example). It is beyond the scope of this technology to explain why this technology can improve upon these existing arts, but in summary, it can greatly increase effective signal strength in 'chroma' oriented digital watermarking applications, and the additional information channels and fidelity thereof can greatly increase signature-characteristics for fingerprinting applications. And gimmick wise, no question, direct graphics can be printed into CMYK objects which can't be seen by normal human vision but sure enough, with a little bit of multi-band distinguishing, come out clear as day in a hyper-spectral image.

Figure 30:
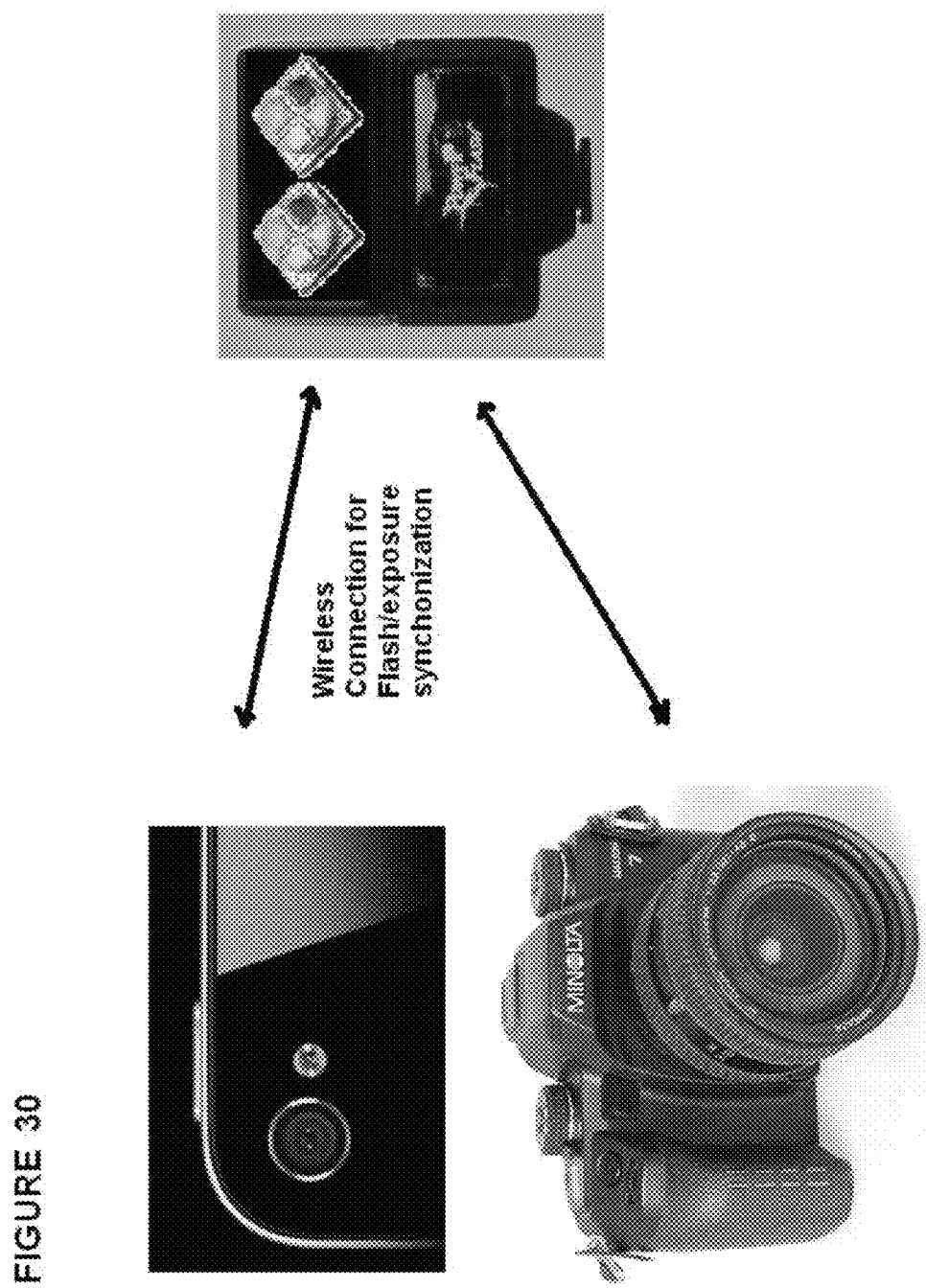
FIG. 30 details how conventional form-factor flash units can employ the present technology.

FIG. 30 just presents the quick note that any and all 'traditional flash units' of any kind could potentially be 'upgraded' to the principles of the technology. The need for frame/flash synchronization can be solved in a variety of ways, including 'post hoc' filtering in cases where there is no wired or wireless way to do direct synchronization. Bottom line: there is a bunch of legacy equipment out there that with a little cleverness can be morphed in this technology's direction.

FIG. 31 makes the point that integrating a properly tuned multi-LED into the actual LED aperture/slot of a smart phone may be practically a few years out, and there are highly viable and faster ways to market with this technology. The depicted smart phone has a not-entirely uncommon 'clip-on' unit, in this case some extra helper-optics, but there is zero reason why this can't be a flash unit instead (or in addition to).

Figure 31A:
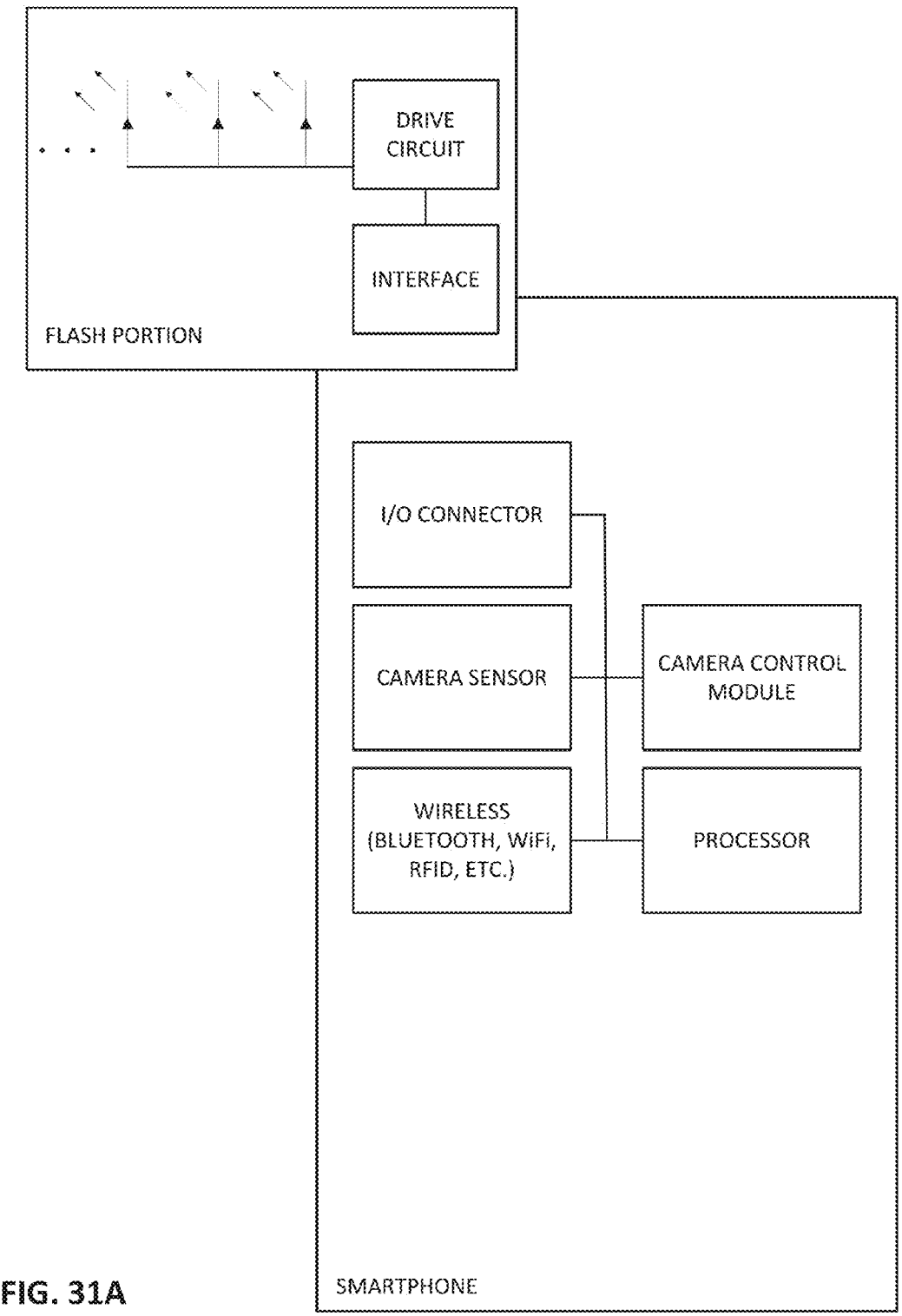

FIG. 31A is a block diagram showing selected components of a smartphone and of such a clip-on accessory. In the phone, a camera control module sends signals to which the camera sensor responds. Among these signals is a frame timing control signal, which triggers the sensor to capture a frame of image data, e.g., in a video sequence. The accessory includes an interface portion that receives a version of this frame timing signal from the camera. Based on this information concerning the timing of frame capture, a drive circuit in the accessory controls illumination of selected LEDs in a programmed, synchronized manner.

In one particular implementation, the clip-on accessory plugs into an I/O connector on the phone. For example, the multi-pin connector at the bottom of the Apple iPhone device may be used, or the signal jack through which audio signals are transferred between the device and peripherals can be used. In the latter case, the flash accessory may be programmed in accordance with audio signals provided to the accessory under control of the smartphone processor. The flash unit can interpret the frequencies and timings of these audio signals as specifying flashes of different LEDs, of different intensities, and of different durations, in successive video frame capture intervals.

In another arrangement, the interface receives the frame timing signal by a wireless connection, such as RFID or Bluetooth or WiFi. In yet another arrangement, a signal is conveyed from the smartphone to the flash accessory by a wired connection.

Power for the flash unit may be provided from the smartphone (e.g., via a wired connection), or the unit may have its own battery power source.

While the flash accessory in the depicted arrangements is adapted to physically engage a portion of the smartphone, so as to removably attach to the smartphone, in other embodiments the flash components can be integrated into the smartphone.

FIG. 32 quickly treats the important practical issue of motion. Motion of both the camera relative to a scene, but also motion in terms of video. This disclosure has touched upon video mainly as a 'flashing' and frame reconstruction issue, this figure looks more at the raw motion of the camera frame relative to some external scene. The somewhat mature technology of 'motion compensation' is explicitly called out in the figure, where many companies and camera suppliers have already solved basic problems of what many call 'motion blur.' (This problem is also addressed in applicant's application 61/759,996.) Point number one here is: use them. The figure keys more in on the ideas that different frame exposures correspond to different spectral flashes as a general matter. So, there are then ways to tap into standard motion estimation of the frame relative to a scene, these same approaches can be applied to the luminance element of all frames—their general structure of brightness variations, to then ultimately re-associate the pixel patches from one flash image to another flash image. Image X may need to shift a couple pixels up and over to some master reference frame, and image Y may need to do the opposite. These operations are fairly well known in image processing, mainly dealing with image registration and also 'orthographic alignment,' with the end result always being improved resilience to performance degradation due to motion. This area also fits well into the proprietary methods bucket, where practitioners of the technology are highly encouraged to invent improved image registration methods.

Light Tweaking

Figure 33:
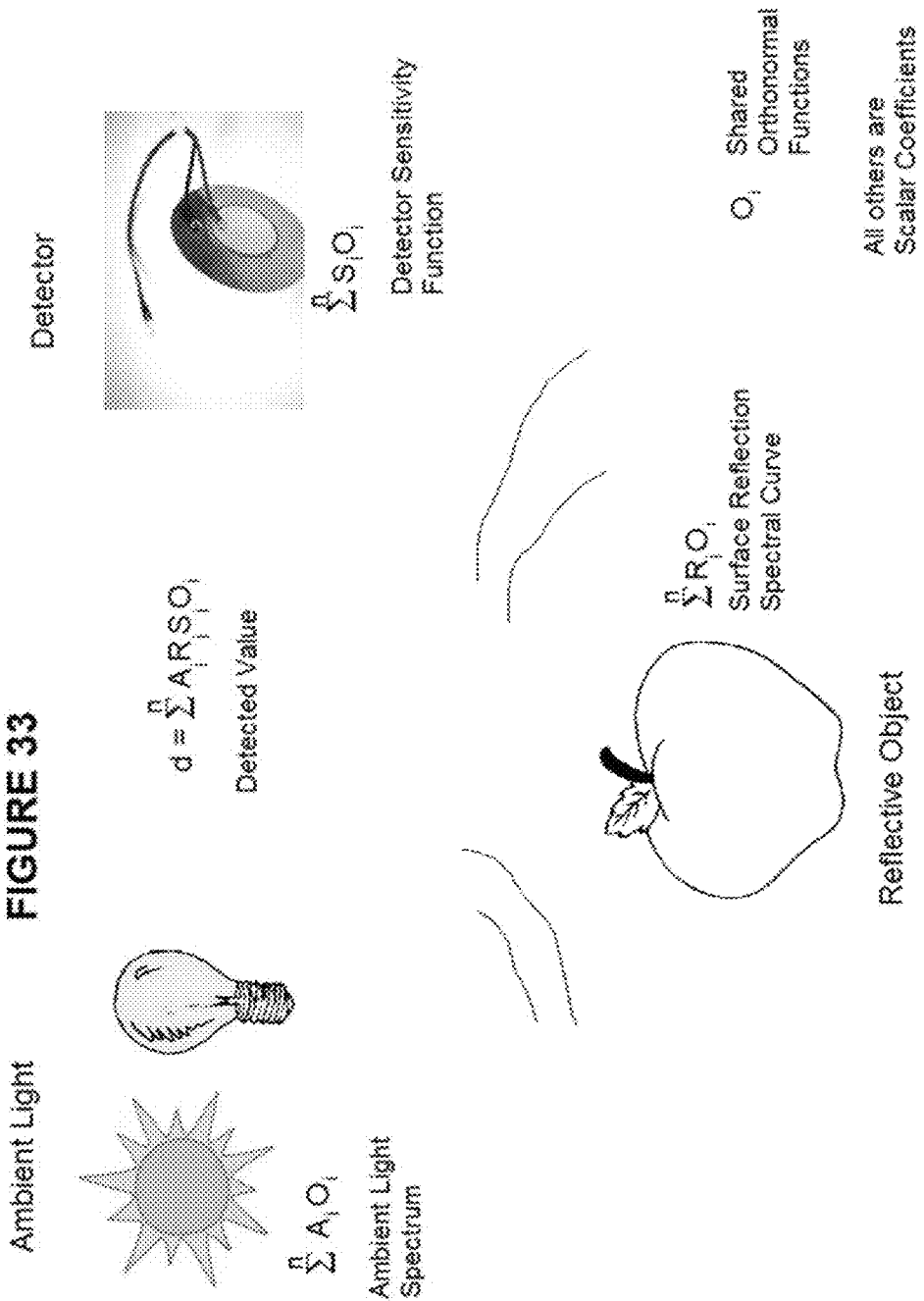
FIGS. 33-36 further elaborate considerations involving ambient lighting.

FIG. 33 attempts to describe from a more mathematical angle how arbitrary ambient lighting can be dealt with and mitigated in terms of its effects on the measurement of surface spectral characteristics and/or surface color. The mathematical treatment then culminates in a more detailed 'routine' that can be applied to the issue of ambient-lighting correction. This routine will be referred to as light tweaking.

In FIG. 33 we find light sources (representing 'ambient' light) with some arbitrary spectral profile represented as a set of coefficients multiplying some orthonormal set of bases functions defined from 400 nm to 700 nm. We see this light source uniformly lighting some flat and uniform surface with a reflectance spectral profile with its own set of coefficients using the same orthonormal bases functions. Then we see a single photodetector measuring the reflected light from the surface, where the spectral response of the detector has yet a third set of coefficients describing its properties, again using the same bases functions. Those practiced in illumination and light detection arts can appreciate the generalizations in the extreme represented in this figure. This is very deliberate so that light tweaking can be clearly defined and seen instantly by artisans to be viable.

Figure 34:
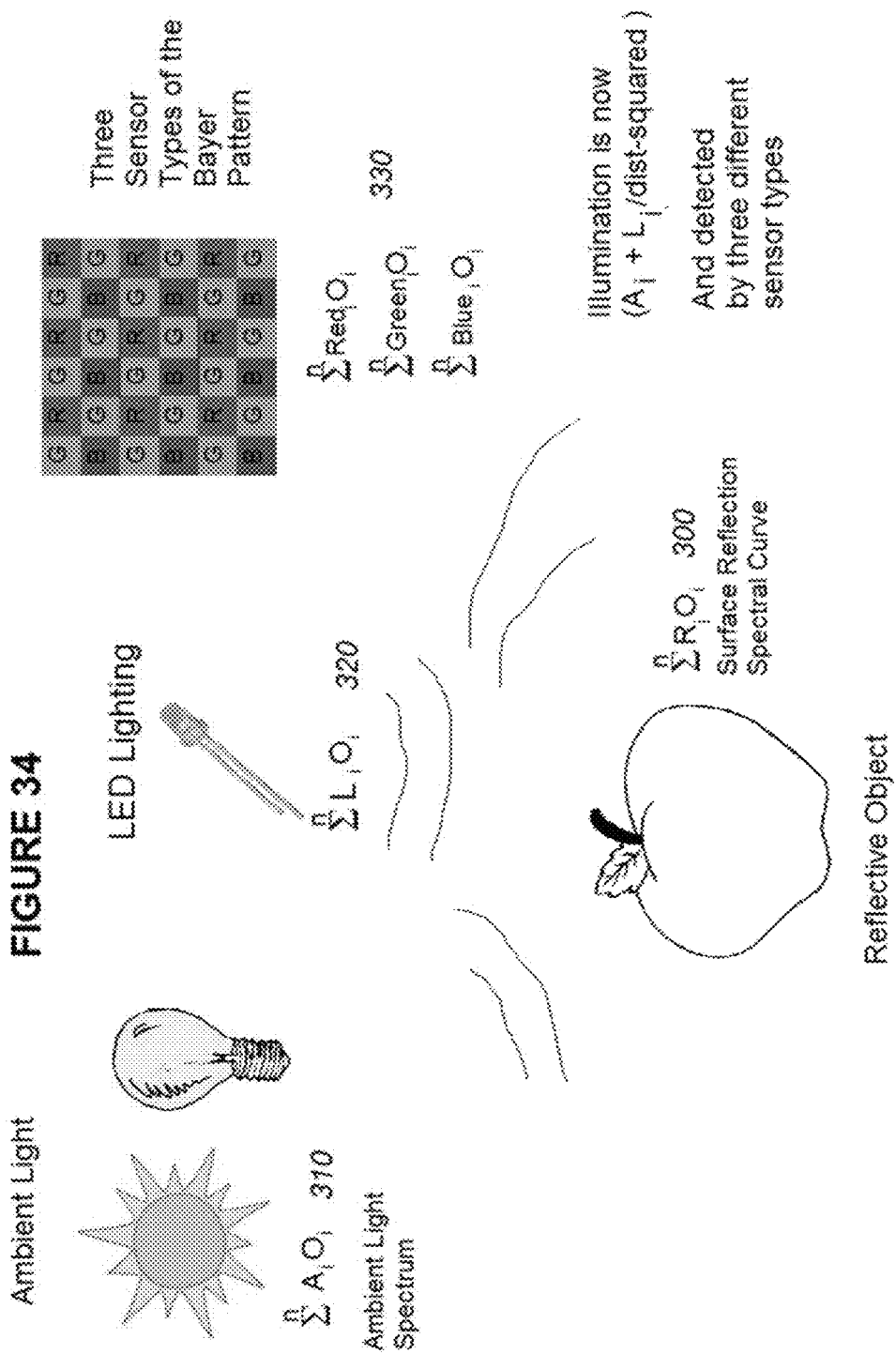

FIG. 34 now introduces a fourth set of spectral coefficients belonging to an LED (or equivalent) second light source also uniformly lighting the surface. Depicted with this new LED source is the need to be more specific about distance between a source and an object than with 'ambient.' For the purposes of measuring 'relative spectral reflectance' of surfaces, all spectral components of the LED lighting will experience the same distance-squared diminution, and hence distance is merely a formal factor which requires noting for a full mathematical treatment but which can easily be dealt with in the measurement solution process. We also see three detectors now instead of one, where all three have differing spectral sensitivity functions and in this particular embodiment, they take on the spectral profiles typical of Bayer-pattern imaging detectors or R, G and B. The task to be defined and then solved is to determine the unknown surface spectral coefficients, 300, given the unknown ambient coefficients 310, and the known spectral coefficients 320 and 330. More particularly, the task will be to make this measurement even when the light energy from the LED source is dwarfed by the ambient light energy, perhaps up to where the ambient light is fully ten times brighter than the LED light reaching the surface, and perhaps even brighter. Ultimate brightness ratios and measurement signal to noise properties reduce to classic empirical testing, where additional disclosure will show that once thousands and millions of Bayer pixels are sampling surfaces multiple times per second, superb surface spectral measurements become possible. The same 'routine' certainly applies to non-Bayer spectral sensitivity pixels and non-LED known light source illuminators and much more complicated ambient lighting conditions than that depicted in FIG. 33.

FIG. 35 now expands the number of LED light sources to 4, from just the 1 in FIG. 34. Not unsurprisingly each LED has its own spectral radiance profile characterized by coefficients 340. For this point in the disclosure's description of the 'routine,' FIG. 35 can represent the state where all LED elements are turned off and hence all L1, L2, L3 and L4 individual spectral coefficients are zero. The next few paragraphs and figures then describe the 'tweaking' by this four element LED unit, in contrast to this completely off state of FIG. 35.

FIG. 36 now introduces an individual tweak of light tweaking. LED 1 is turned full on during a sampling exposure of the 3 R, G and B pixels. The sampling duration (exposure time) is identical to that of FIG. 35. FIG. 36 shows that there are now new measured values from the three pixels, 350. For explanatory purposes, these values are only slightly higher than those of FIG. 35 so that we can immediately illustrate that the LED lighting can be much weaker than ambient lighting and yet as we will see, good surface spectral measurements can nonetheless be made. Label 360 indicates this by putting the explicit distance fall-off term into the figure, where we can imagine that the LED contribution might be 10% or even less than the ambient contribution.

The light tweaking routine then posits that a 5 frame period cycling of pulsing the individual LED sources, including a single 'all off' state, can illuminate the surface. This cycling would be designed to be in perfect synchrony to the frame rate of a conventional Bayer-pattern imaging device (or any monochrome of multi-spectral imaging device as well). Each frame would isolate some given state of supplemental (to ambient) LED illumination, including no supplemental illumination at all. The ensuing mathematical formalism of this cycling can also be depicted in FIG. 36 if we substitute the appropriate L coefficients into the equations 350, including zeros for the all-off state of the 5 cycles.

FIG. 37 explicitly shows how the unknown ambient lighting spectral coefficients can quite easily be removed from the aggregate mathematical equations. In practice, everyone knows cameras move and surfaces move, but by cycling the 'no illumination' state along with the LED tweaked states, a constant sampling of pure-ambient values can take place and interpolated into the time periods where the tweaked states are occurring.

Straightforward simultaneous linear equations fall out isolating the unknown surface coefficients in a classic 'f' vector, modulated as they are by the 'known' tweak values of the LED coefficients and R, G and B, represented by the classic H matrix, then finally the measured del-R, del-G and del-B values themselves become the classic 'g' vector, all rolled up as a g=Hf standard linear algebraic equation. f=inverse H times g is the equally classic solution to this equation, with over a century of prior art methods applicable to properly forming, filtering and shaping such solutions generally with the goal of optimizing signal to noise ratios on the measurement of surface reflectance coefficients. [Note that an additional 'unknown' is present—the precise ratio of overall ambient light to the LED light; solutions can be formed with this additional unknown, or, there are methods such as depth-sensing which can aid in independently measuring this unknown for applications where this might benefit the overall measurement fidelity; the g=Hf formulation implicitly contains this distance factor and it is only in highly mobile situations where this additional distance nuance needs to be worried about as an error component on measurements due to motion].

This section's discussion up through FIG. 37 posits a very simple lighting situation, a simple surface, uniform lighting and only three detectors whereas modern imaging devices usually have millions of such RGB detectors. Be this as it may, these simple principles are quite extensible to small patches of imaging sensors viewing small pseudo-uniform patches of objects and their surfaces. Ambient lighting conditions can vary quite a bit on 'normal' objects and scenes, especially with regards to surface normal (perpendicular directions from the surface) relative to where a camera is placed. Applications will range from extremes where surfaces change their characteristics on a 'per pixel region' basis, all the way to broad uniformly lit surfaces giving rise to near-identical measurement conditions across millions of pixels (think placing a camera up close to a flat color of some graphic printed paper or package). It is thus entirely expected that these principles described in FIGS. 33-37 will adapt accordingly. Where certain levels of 'region uniformity' are discovered, thousands and millions of R, G and B measurements per second can be classically averaged together prior to submittal to the g=Hf solution formalism, culminating into excellent surface spectral measurements even when the LED lighting is 10× fainter, or even fainter, than ambient lighting.

Counterfeit 'Suspection'

Using the present technology, ink and other manufactured surfaces will be found to have distinctive 'spectral signatures' that can be used to separate originally printed, authentic articles from counterfeited articles. The non-English word 'Suspection' is used in the title, though those practiced in the art of counterfeit analysis may substitute 'detection' as well. There is a subtle yet slightly arcane reason suspicion is used rather than detection: purists understand that unequivocal 'detection' of counterfeits is an asymptotic goal and never (in practice) an achievable absolute. A milder form of a technical goal is then to strongly suspect something to be counterfeit and then to either believe that suspicion if its integrity is sufficiently high, or, to subject some suspected counterfeit article to further testing for authenticity.

A counterfeit suspicion device can consist of a clip-on unit similar to FIG. 31. A local or internet library of spectral signatures for various articles is stored, and when some given article is 'scanned' by the device and a spectral signature thus generated, a comparison with stored signatures is made, with some threshold set separating 'apparently authentic' versus 'suspected as counterfeit.'

Specific choices of LED illumination spectral ranges can also be tuned and selected to help discriminate between originals and counterfeits. For example, a specific ink might be chosen which might have very strong reflective properties around 610 nanometers, and then one of the LED choices for illumination may similarly have strong illumination at 610 nanometers. The strong signal picked up from this concurrence of spectra would assist in separating originals from counterfeits in the ensuing spectral measurement processes.

Multiple phases of illumination and analysis can be conducted—each yielding further evidence tending to indicate that a suspect item is or is not a counterfeit.

To review, one aspect of the present technology comprises a flash accessory for use with a smartphone, where the smartphone is equipped with a camera for capture of a multi-frame video sequence. The accessory includes a housing including a portion adapted to engage a portion of the smartphone, thereby enabling the accessory to be removably attached to the smartphone. This housing contains plural light emitting diodes having different spectral characteristics; an interface adapted to receive a frame timing control signal from the smartphone; and drive circuitry coupled to said interface, and configured to independently control said plural light emitting diodes. In such arrangement, the drive circuitry is adapted to respond to the frame timing control signal to controllably illuminate different ones of said light emitting diodes in a programmed sequence, at times corresponding to captures of different frames of a video sequence by the smartphone camera.

In one particular such accessory, the interface is adapted to receive an audio frame timing control signal from the smartphone. In another, the interface is adapted to receive a wireless frame timing control signal from the smartphone.

Another aspect of the technology is a smartphone comprising a body; a camera portion for capture of a multi-frame video sequence; a flash portion, including plural light emitting diodes having different spectral characteristics; and drive circuitry configured to independently control the plural light emitting diodes of the flash portion. In such arrangement, the drive circuitry is adapted to controllably illuminate different ones of said light emitting diodes in a programmed sequence, at times corresponding to captures of different frames of a video sequence by the camera portion.

Concluding Remarks

Applicant's other work concerning imaging systems is detailed, e.g., in patent publications 20110212717, 20110161076, 20120284012, 20120218444, 20120046071, and in pending application Ser. No. 13/978,108, filed Oct. 12, 2012, Ser. No. 13/750,752, filed Jan. 25, 2013, and 61/759,996, filed Feb. 1, 2013.

Chrominance-based digital watermarking is detailed, e.g., in the just-cited application Ser. No. 13/750,752, and in U.S. patent documents 20100150434, U.S. Pat. Nos. 6,590,996 and 8,401,224.

While reference has been made to smart phones, it will be recognized that this technology finds utility with all manner of devices—both portable and fixed. Tablets, laptop computers, digital cameras, wrist- and head-mounted systems and other wearable devices, etc., can all make use of the principles detailed herein. (The term "smart phone" should be construed herein to encompass all such devices, even those that are not telephones.)

Particularly contemplated smart phones include the Apple iPhone 5; smart phones following Google's Android specification (e.g., the Galaxy S III phone, manufactured by Samsung, the Motorola Droid Razr HD Maxx phone, and the Nokia N900), and Windows 8 mobile phones (e.g., the Nokia Lumia 920).

Among the Android options, the Nokia N900 is usable with the open source FCam software for programmatic computer camera control. This is advantageous because the FCam technology can be called to cause a camera take certain actions that might be useful in a particular analysis.

Details of the Apple iPhone, including its touch interface, are provided in Apple's published patent application 20080174570.

The design of smart phones and other computers referenced in this disclosure is familiar to the artisan. In general terms, each includes one or more processors, one or more memories (e.g. RAM), storage (e.g., a disk or flash memory), a user interface (which may include, e.g., a keypad, a TFT LCD or OLED display screen, touch or other gesture sensors, a camera or other optical sensor, a compass sensor, a 3D magnetometer, a 3-axis accelerometer, a 3-axis gyroscope, one or more microphones, etc., together with software instructions for providing a graphical user interface), interconnections between these elements (e.g., buses), and an interface for communicating with other devices (which may be wireless, such as GSM, 3G, 4G, CDMA, WiFi, WiMax, Zigbee or Bluetooth, and/or wired, such as through an Ethernet local area network, a T-1 internet connection, etc.).

The processes and system components detailed in this specification may be implemented as instructions for computing devices, including general purpose processor instructions for a variety of programmable processors, including microprocessors (e.g., the Intel Atom, ARM A5, and nVidia Tegra 4; the latter includes a CPU, a GPU, and nVidia's Chimera computational photography architecture), graphics processing units (GPUs, such as the nVidia Tegra APX 2600), and digital signal processors (e.g., the Texas Instruments TMS320 and OMAP series devices), etc. These instructions may be implemented as software, firmware, etc. These instructions can also be implemented in various forms of processor circuitry, including programmable logic devices, field programmable gate arrays (e.g., the Xilinx Virtex series devices), field programmable object arrays, and application specific circuits—including digital, analog and mixed analog/digital circuitry. Execution of the instructions can be distributed among processors and/or made parallel across processors within a device or across a network of devices. Processing of data may also be distributed among different processor and memory devices. As noted, cloud computing resources can be used as well. References to "processors," "modules" or "components" should be understood to refer to functionality, rather than requiring a particular form of implementation.

Software instructions for implementing the detailed functionality can be authored by artisans without undue experimentation from the descriptions provided herein, e.g., written in C, C++, Visual Basic, Java, Python, Tcl, Perl, Scheme, Ruby, etc. Smartphones and other devices according to certain implementations of the present technology can include software modules for performing the different functions and acts.

Known browser software, communications software, imaging software, and media processing software can be adapted for use in implementing the present technology.

Software and hardware configuration data/instructions are commonly stored as instructions in one or more data structures conveyed by tangible media, such as magnetic or optical discs, memory cards, ROM, etc., which may be accessed across a network. Some embodiments may be implemented as embedded systems—special purpose computer systems in which operating system software and application software are indistinguishable to the user (e.g., as is commonly the case in basic cell phones). The functionality detailed in this specification can be implemented in operating system software, application software and/or as embedded system software.

Different of the functionality can be implemented on different devices. Thus, it should be understood that description of an operation as being performed by a particular device (e.g., a smart phone) is not limiting but exemplary; performance of the operation by another device (e.g., a remote server), or shared between devices, is also expressly contemplated.

(In like fashion, description of data being stored on a particular device is also exemplary; data can be stored anywhere: local device, remote device, in the cloud, distributed, etc.)

This specification has discussed several different embodiments. It should be understood that the methods, elements and concepts detailed in connection with one embodiment can be combined with the methods, elements and concepts detailed in connection with other embodiments. While some such arrangements have been particularly described, many have not—due to the large number of permutations and combinations. However, implementation of all such combinations is straightforward to the artisan from the provided teachings.

Elements and teachings within the different embodiments disclosed in the present specification are also meant to be exchanged and combined.

While this disclosure has detailed particular ordering of acts and particular combinations of elements, it will be recognized that other contemplated methods may re-order acts (possibly omitting some and adding others), and other contemplated combinations may omit some elements and add others, etc.

Although disclosed as complete systems, sub-combinations of the detailed arrangements are also separately contemplated (e.g., omitting various of the features of a complete system).

While certain aspects of the technology have been described by reference to illustrative methods, it will be recognized that apparatuses configured to perform the acts of such methods are also contemplated as part of applicant's inventive work. Likewise, other aspects have been described by reference to illustrative apparatus, and the methodology performed by such apparatus is likewise within the scope of the present technology. Still further, tangible computer readable media containing instructions for configuring a processor or other programmable system to perform such methods is also expressly contemplated.

The present specification should be read in the context of the cited references. (The reader is presumed to be familiar with such prior work.) Those references disclose technologies and teachings that the inventors intend be incorporated into embodiments of the present technology, and into which the technologies and teachings detailed herein be incorporated.

To provide a comprehensive disclosure, while complying with the statutory requirement of conciseness, applicant incorporates-by-reference each of the documents referenced herein. (Such materials are incorporated in their entireties, even if cited above in connection with specific of their teachings.)

In view of the wide variety of embodiments to which the principles and features discussed above can be applied, it should be apparent that the detailed embodiments are illustrative only, and should not be taken as limiting the scope of the invention. Rather, we claim as our invention all such modifications as may come within the scope and spirit of the following claims and equivalents thereof.

The invention claimed is:

1. A flash accessory for use with a smartphone, the smartphone being equipped with a camera for capture of a multi-frame video sequence, the accessory comprising:
    a housing including a portion adapted to engage a portion of the smartphone, thereby enabling the accessory to be removably attached to the smartphone, the housing containing:
    plural light emitting diodes having different spectral characteristics;
    an interface adapted to receive an audio frame timing control signal from the smartphone; and
    drive circuitry coupled to said interface, and configured to independently control said plural light emitting diodes;
    wherein the drive circuitry is adapted to respond to the audio frame timing control signal to controllably illuminate different ones of said light emitting diodes in a programmed sequence, at times corresponding to captures of different frames of a video sequence by the smartphone camera.

2. A method of operating a smartphone that includes a camera portion and a flash unit, the camera portion including a CMOS sensor comprised of rows and columns of pixels, and a color filter arrangement comprising elements of three different filter colors, to yield frames of imagery having three different color channels, the flash unit including plural LEDs with N different illumination spectra, where N is at least four, the method comprising the acts:
    using said camera portion, capturing a plural-frame video sequence depicting a patch of an object surface;
    operating the flash unit in a programmed sequence to controllably illuminate the patch with differently-colored illumination from said LEDs, at times corresponding to captures of different frames of the video sequence by the camera portion, wherein:
        during capture of a first frame of the video sequence, an LED with a first of said N spectra is illuminated;
        during capture of a second frame of the video sequence, an LED with a second of said N spectra is illuminated;
        during capture of a third frame of the video sequence, an LED with a third of said N spectra is illuminated;
        during capture of a fourth frame of the video sequence, an LED with a fourth of said N spectra is illuminated;
    the method further include processing frames including said first through fourth frames of the video sequence to yield spectral profile data for said patch in more than N different visible-light spectral bands, due to coupling between said N different illumination spectra, and plural of said different color channels.

3. The method of claim 2 wherein, during capture of a fifth frame of the video sequence, none of said LEDs is illuminated, the method further including processing frames including said first through fifth frames of the video sequence to yield ambient light-compensated spectral profile data for said patch in said more than N different visible-light spectral bands.

4. The method of claim 2 that further includes:
operating an LED having a first of said N spectra at one non-zero intensity in the first frame, and at a different non-zero intensity in a fifth frame;
operating an LED having a second of said N spectra at one non-zero intensity in the second frame, and at a different non-zero intensity in a sixth frame;
operating an LED having a third of said N spectra at one non-zero intensity in the third frame, and at a different non-zero intensity in a seventh frame; and
operating an LED having a fourth of said N spectra at one non-zero intensity in the fourth frame, and at a different non-zero intensity in an eighth frame.

5. The method of claim 4 that includes processing frames including said first through eighth frames of the video sequence to yield ambient light-compensated spectral profile data for said patch in said more than N different visible-light spectral bands.

6. The method of claim 2 wherein said more than four different visible-light spectral bands include at least two bands of different spectral widths.

7. The method of claim 2 wherein said flash unit is an accessory flash unit that is removably attached to a body of the smartphone, the method further including providing control signals to said accessory flash unit from an audio signal jack of said smartphone.

8. A smartphone comprising:
a body;
a camera portion, for capture of a multi-frame video sequence depicting a patch of an object surface;
a flash portion, including plural light emitting diodes having different spectral characteristics; and
drive circuitry configured to independently control said plural light emitting diodes of the flash portion;
wherein the drive circuitry is adapted to controllably illuminate different ones of said light emitting diodes in a programmed sequence, at times corresponding to captures of different frames of a video sequence by the camera portion; and
wherein the camera portion comprises a CMOS sensor having rows and columns of pixels, the camera portion further including a color filter arrangement comprising elements of three different filter colors to yield imagery having three different color channels, and wherein the drive circuitry is adapted to:
illuminate a light emitting diode with a first of said different spectral characteristics, during capture of a first frame of the video sequence;
illuminate a light emitting diode with a second of said different spectral characteristics, during capture of a second frame of the video sequence;
illuminate a light emitting diode with a third of said different spectral characteristics, during capture of a third frame of the video sequence;
illuminate a light emitting diode with a fourth of said different spectral characteristics, during capture of a fourth frame of the video sequence;
the smartphone further including a processor configured to process frames including said first through fourth frames of the video sequence to yield spectral profile data for said patch in more than four different visible-light spectral bands, due to coupling between said plural different spectral characteristics of the light emitting diodes, and plural of said different color channels.

9. The smartphone of claim 8 in which the drive circuitry is adapted to illuminate none of said light emitting diodes, during capture of a fifth image frame, and in which said processor is configured to process frames including said first through fifth frames of the video sequence to yield ambient light-compensated spectral profile data for said patch in said more than four different visible-light spectral bands.

10. The smartphone of claim 8 in which the drive circuitry is adapted to:
illuminate a light emitting diode with the first of said different spectral characteristics, during capture of a fifth frame of the video sequence;
illuminate a light emitting diode with the second of said different spectral characteristics, during capture of a sixth frame of the video sequence;
illuminate a light emitting diode with the third of said different spectral characteristics, during capture of a seventh frame of the video sequence;
illuminate a light emitting diode with the fourth of said different spectral characteristics, during capture of an eighth frame of the video sequence; and
in which said processor is configured to process frames including said first through eighth frames of the video sequence to yield ambient light-compensated spectral profile data for said patch in said more than four different visible-light spectral bands.

11. The smartphone of claim 8 wherein said more than four different visible-light spectral bands include at least two bands of different spectral widths.

12. A smartphone comprising:
a body;
a camera portion, for capture of a multi-frame video sequence;
a flash portion, including plural light emitting diodes having different spectral characteristics; and
drive circuitry configured to independently control said plural light emitting diodes of the flash portion;
wherein the drive circuitry is adapted to controllably illuminate different ones of said light emitting diodes in a programmed sequence, at times corresponding to captures of different frames of a video sequence by the camera portion;
wherein said flash portion is an accessory flash unit that is removably attached to a body of the smartphone, and the smartphone includes a signal link conveying control signals to said accessory flash unit from an audio signal jack of the smartphone.

* * * * *